(12) United States Patent
Hazama et al.

(10) Patent No.: US 11,083,467 B2
(45) Date of Patent: Aug. 10, 2021

(54) HEMOSTATIC DEVICE

(71) Applicant: TERUMO KABUSHIKI KAISHA, Tokyo (JP)

(72) Inventors: Kenichi Hazama, Bear, DE (US); Ryosuke Maeda, Fujinomiya (JP); Junichi Kobayashi, Fuji (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 204 days.

(21) Appl. No.: 16/238,295

(22) Filed: Jan. 2, 2019

(65) Prior Publication Data
US 2019/0133605 A1 May 9, 2019

Related U.S. Application Data

(63) Continuation of application No. PCT/JP2017/024388, filed on Jul. 3, 2017.

(30) Foreign Application Priority Data

Jul. 6, 2016 (JP) .............................. JP2016-134606

(51) Int. Cl.
*A61B 17/12* (2006.01)
*A61B 17/135* (2006.01)
(Continued)

(52) U.S. Cl.
CPC ...... *A61B 17/135* (2013.01); *A61B 17/12009* (2013.01); *A61B 17/1325* (2013.01);
(Continued)

(58) Field of Classification Search
CPC ............ A61B 17/135; A61B 17/12009; A61B 17/1325; A61B 17/12; A61B 2017/00637;
(Continued)

(56) References Cited

U.S. PATENT DOCUMENTS

2007/0191881 A1* 8/2007 Amisar ............. A61B 17/1325
606/203

FOREIGN PATENT DOCUMENTS

| CN | 105147353 A | 12/2015 |
|---|---|---|
| CN | 205286445 U | 12/2015 |

(Continued)

OTHER PUBLICATIONS

International Search Report (PCT/ISA/210) dated Oct. 10, 2017, by the Japan Patent Office as the International Searching Authority for International Application No. PCT/JP2017/024388.
(Continued)

*Primary Examiner* — Erich G Herbermann
(74) *Attorney, Agent, or Firm* — Buchanan Ingersoll & Rooney PC

(57) ABSTRACT

A hemostatic device includes a band for wrapping around a puncture site of a wrist, a mechanism for securing the band to the wrist in a wrapped state, an inflatable portion connected to the band and inflated by being injected with air, a tube body that communicates between an inflatable space of the inflatable portion and an outside, and a cover portion that covers the tube body in the inflatable portion, in which the tube body has a hole portion that opens in the inflatable portion, the cover portion has a communication portion that is disposed to cover the hole portion and allows communication between the hole portion and the inflatable portion by being positioned to overlap the hole portion, and the tube body is movable relative to the cover portion so that a positional relation between the communication portion and the hole portion is controllable.

13 Claims, 15 Drawing Sheets

(51) Int. Cl.
*A61B 17/132* (2006.01)
*A61B 17/00* (2006.01)

(52) U.S. Cl.
CPC ............... *A61B 2017/00637* (2013.01); *A61B 2017/12004* (2013.01); *A61B 2017/12018* (2013.01); *A61L 2400/04* (2013.01)

(58) Field of Classification Search
CPC A61B 2017/12004; A61B 2017/12018; A61B 5/02233; A61L 2400/04; A61F 5/30
See application file for complete search history.

(56) References Cited

FOREIGN PATENT DOCUMENTS

| GB | 2504778 A | 8/2012 |
|---|---|---|
| JP | 50-128991 U | 10/1975 |
| JP | 3031486 U | 11/1996 |
| JP | 2013-078515 A | 5/2013 |
| WO | 2015/199024 A1 | 12/2015 |

OTHER PUBLICATIONS

Written Opinion (PCT/ISA/237) dated Oct. 10, 2017, by the Japan Patent Office as the International Searching Authority for International Application No. PCT/JP2017/024388.
The extended European Search Report dated Oct. 25, 2019, by the European Patent Office in corresponding European Patent Application No. 17824209.5-1122. (8 pages).
An English Translation of the International Search Report (Form PCT/ISA/210) and the Written Opinion of the International Searching Authority (Form PCT/ISA/237) dated Oct. 10, 2017, by the Japanese Patent Office in corresponding International Application No. PCT/JP2017/024388. (6 pages).
Notification of First Office Action issued in Chinese Office Action dated Dec. 2, 2020 regarding Application No. 2017800417844 with English translation, 14 pages.

\* cited by examiner

HEMOSTATIC DEVICE

CROSS-REFERENCE TO RELATED APPLICATIONS

This application is a continuation of International Application No. PCT/JP2017/024338, filed on Jul. 8, 2017, which claims priority to Japanese Patent Application No. 2016-134606, filed on Jul. 6, 2016, the entire content of both being incorporated herein by reference.

TECHNICAL FIELD

The present invention relates to a hemostatic device for performing hemostasis by pressing a punctured site.

BACKGROUND DISCUSSION

Recently, percutaneous treatment/examination, etc. has been performed by puncturing a blood vessel of an arm, a leg, etc., introducing an introducer sheath to a puncture site, and delivering a medical instrument such as a catheter to a lesion through a lumen of the introducer sheath. When such treatment/examination, etc. is performed, an operator needs to perform hemostasis in the puncture site after withdrawing the introducer sheath. To perform hemostasis, there has been a known hemostatic device including a band for wrapping around a limb such as an arm, a leg, etc., means for securing that secures the band in a state of being wrapping around the limb, and an inflatable portion connected to the band to press the puncture site by inflating in response to injection of a fluid.

As described in Japanese Utility Model Application No. 7-7965, when a hemostatic device is used, in general, a doctor or a nurse connects a dedicated instrument such as a syringe separate from the hemostatic device to a port communicating with an inflatable portion of the hemostatic device and injects a fluid into the inflatable portion using the dedicated instrument, thereby inflating the inflatable portion of the hemostatic device.

In a treatment using the hemostatic device, when the inflating inflatable portion continues to strongly press the puncture site and a surrounding blood vessel or nerve for a long time, there is a possibility of causing numbness or pain or occluding the blood vessel.

For example, in the case of using the hemostatic device described in Japanese Utility Model Application No. 7-7965, to prevent vascular occlusion, etc., the doctor or the nurse regularly connects the dedicated instrument such as the syringe to the hemostatic device after inflating the inflatable portion, and discharges a fluid in the inflatable portion. In this way, a pressing force acting on the puncture site is reduced over time by performing a decompression operation of reducing an internal pressure of the inflatable portion.

However, the decompression operation of the hemostatic device of Japanese Utility Model Application No. 7-7965 requires an operation of regularly connecting the dedicated instrument such as the syringe to the hemostatic device, and thus may increase an effort of the doctor or the nurse. In addition, when the dedicated instrument is lost, there is a possibility of occurrence of a situation in which the decompression operation of the inflatable portion of the hemostatic device may not be performed.

There exists a need, therefore, to provide a hemostatic device capable of performing decompression adjustment of an inflatable portion by a simple operation without using a dedicated instrument separate from the hemostatic device.

SUMMARY

A hemostatic device according to an exemplary embodiment of the disclosure herein includes a band for wrapping around a site of a limb where bleeding is to be stopped, means for securing that secures the band to the limb in a wrapped state, an inflatable portion connected to the band and inflated by being injected with gas, a tube body that communicates between a lumen of the inflatable portion and an outside, and a cover portion that covers the tube body in the inflatable portion, wherein the tube body has a hole portion that opens in the inflatable portion, the cover portion has a communication portion that is disposed to cover the hole portion and allows communication between the hole portion and the lumen of the inflatable portion by being positioned to overlap the hole portion, and the tube body is movable relative to the cover portion so that a positional relation between the communication portion and the hole portion is controllable.

In the hemostatic device of the exemplary embodiment, the tube body is configured to be movable relative to the cover portion such that it is possible to adjust the positional relationship between the hole portion of the tube body and the communication portion of the cover portion. When the communication portion and the hole portion are adjusted to overlapping positions, the communication portion allows communication between the lumen of the inflatable portion and the outside to discharge gas in the inflatable portion to the outside. In addition, in a state in which the positions of the communication portion and the hole portion do not overlap each other, the cover portion seals the hole portion to prevent gas from being discharged from the inflatable portion. As described above, according to the disclosure, it is possible to provide the hemostatic device capable of performing decompression adjustment of the inflatable portion by a simple operation of relatively moving the tube body with respect to the cover portion.

DETAILED DESCRIPTION

Figure 1:
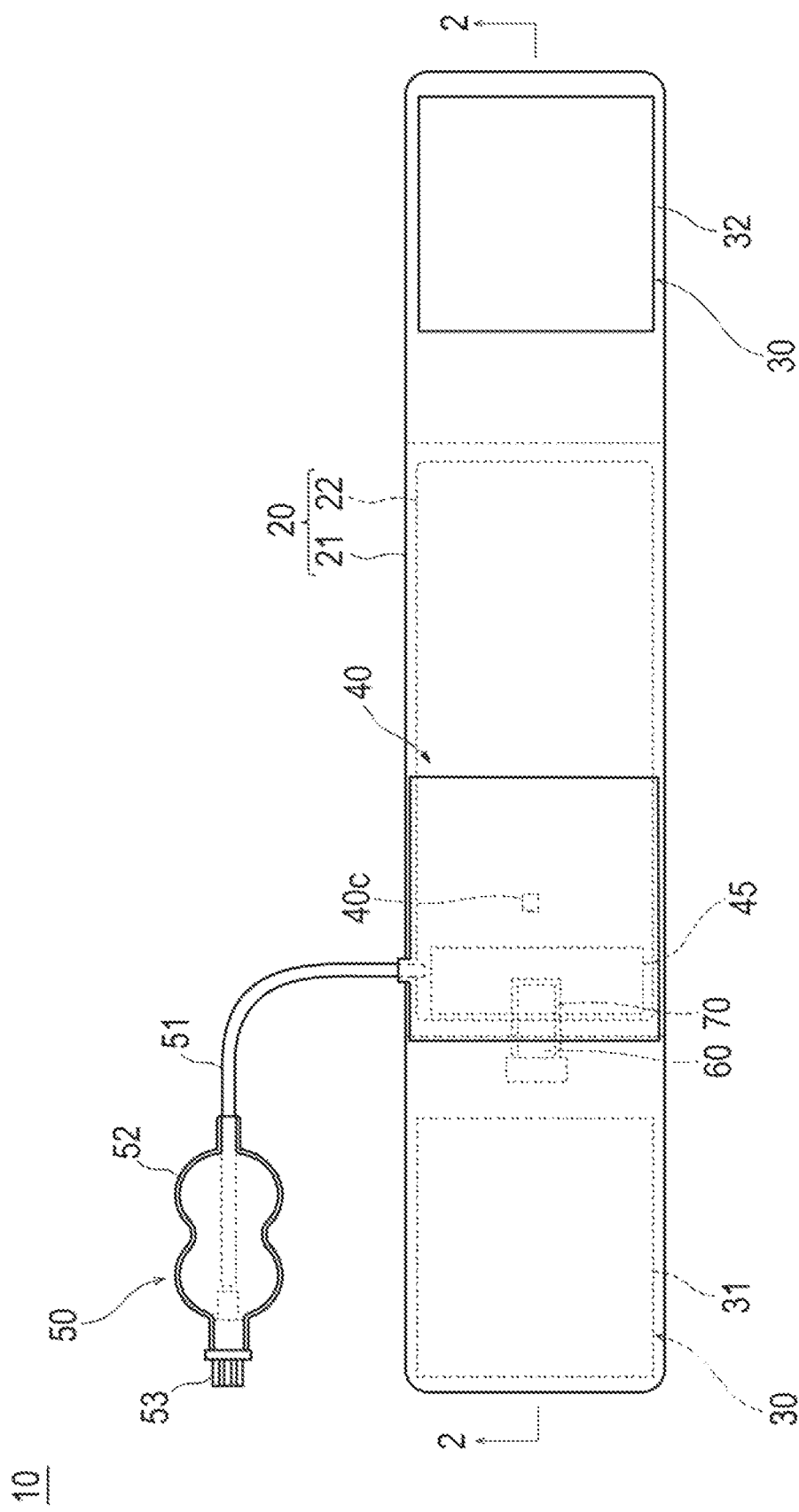
FIG. 1 is a plan view of a hemostatic device according to an exemplary embodiment of the disclosure viewed from an inner surface side.

Hereinafter, an exemplary embodiment of the disclosure and modifications thereof will be described with reference to accompanying drawings. Note that a description below does not restrict a technical scope or a meaning of a term described in the claims. In addition, a ratio of dimensions in the drawings is exaggerated for convenience of description and may be different from an actual ratio.

Figure 4A:
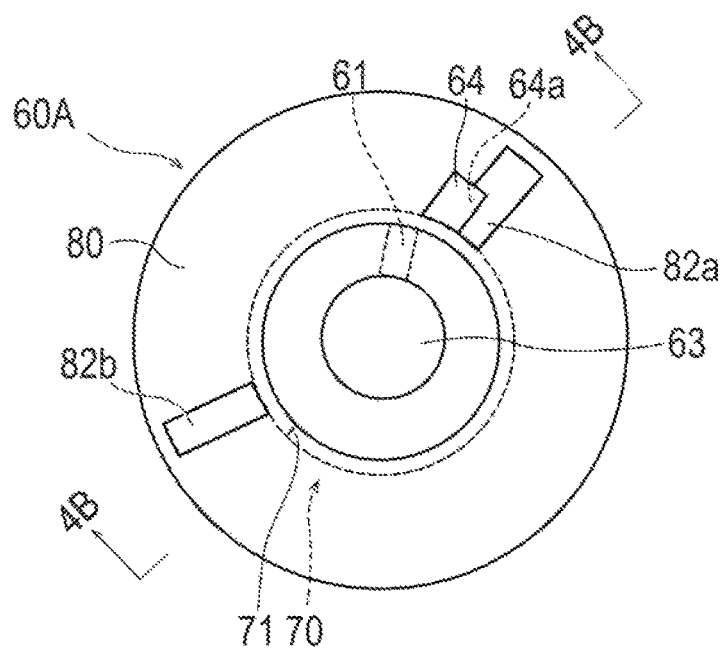
FIG. 4(A) is a plan view of the tube body and the cover portion.
Figure 5A:
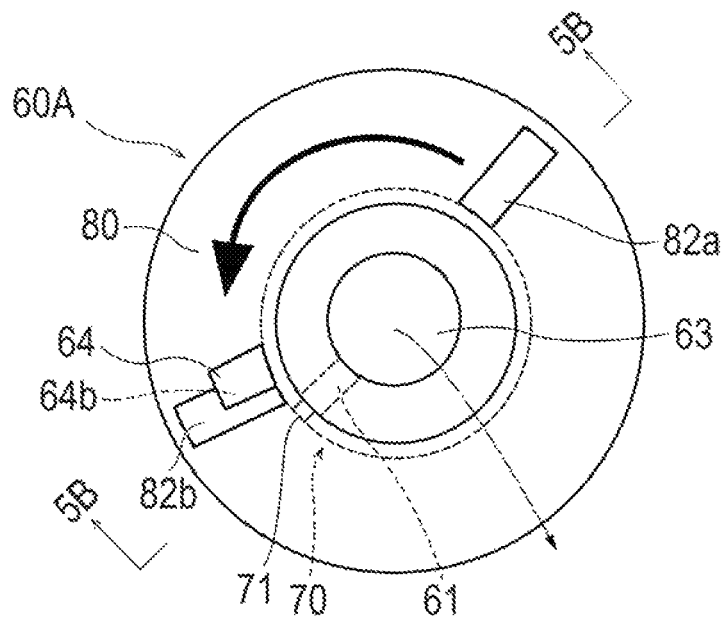
FIG. 5(A) is a plan view of the tube body and the cover portion.
Figure 6:
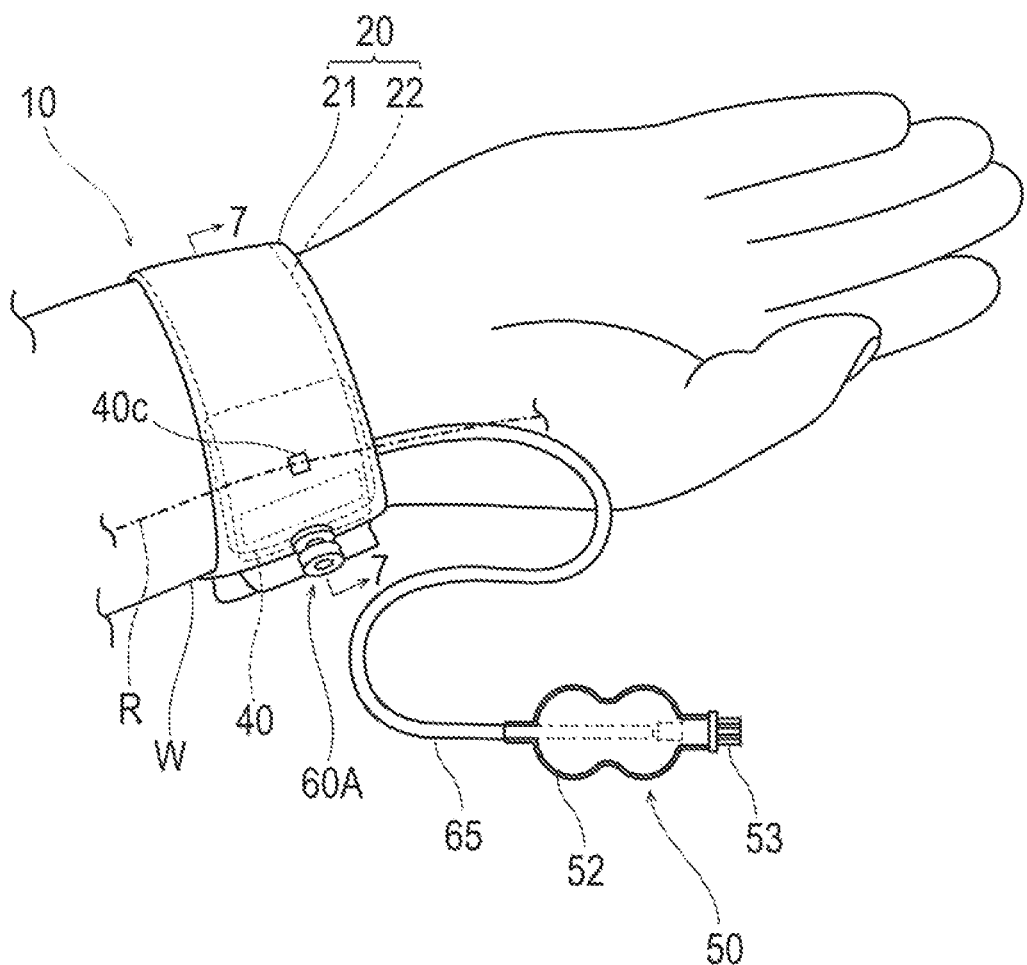
FIG. 6 is a perspective view illustrating a state in which the hemostatic device according to the exemplary embodiment of the disclosure is mounted on a wrist.
Figure 7:
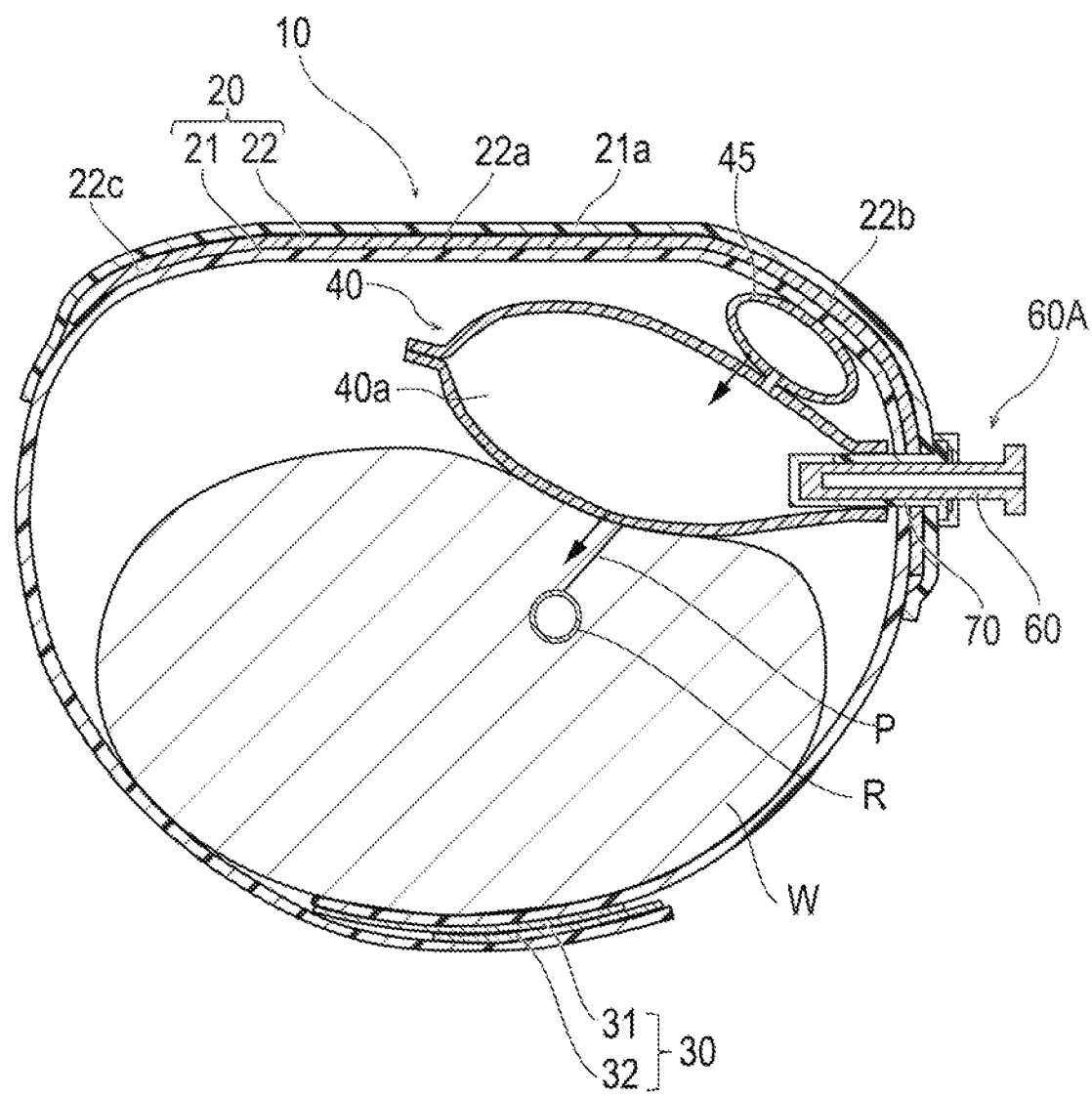
FIG. 7 is a cross-sectional view taken along 7-7 line of FIG. 6 and is a diagram illustrating a state in which an inflatable portion is inflated.
Figure 8:
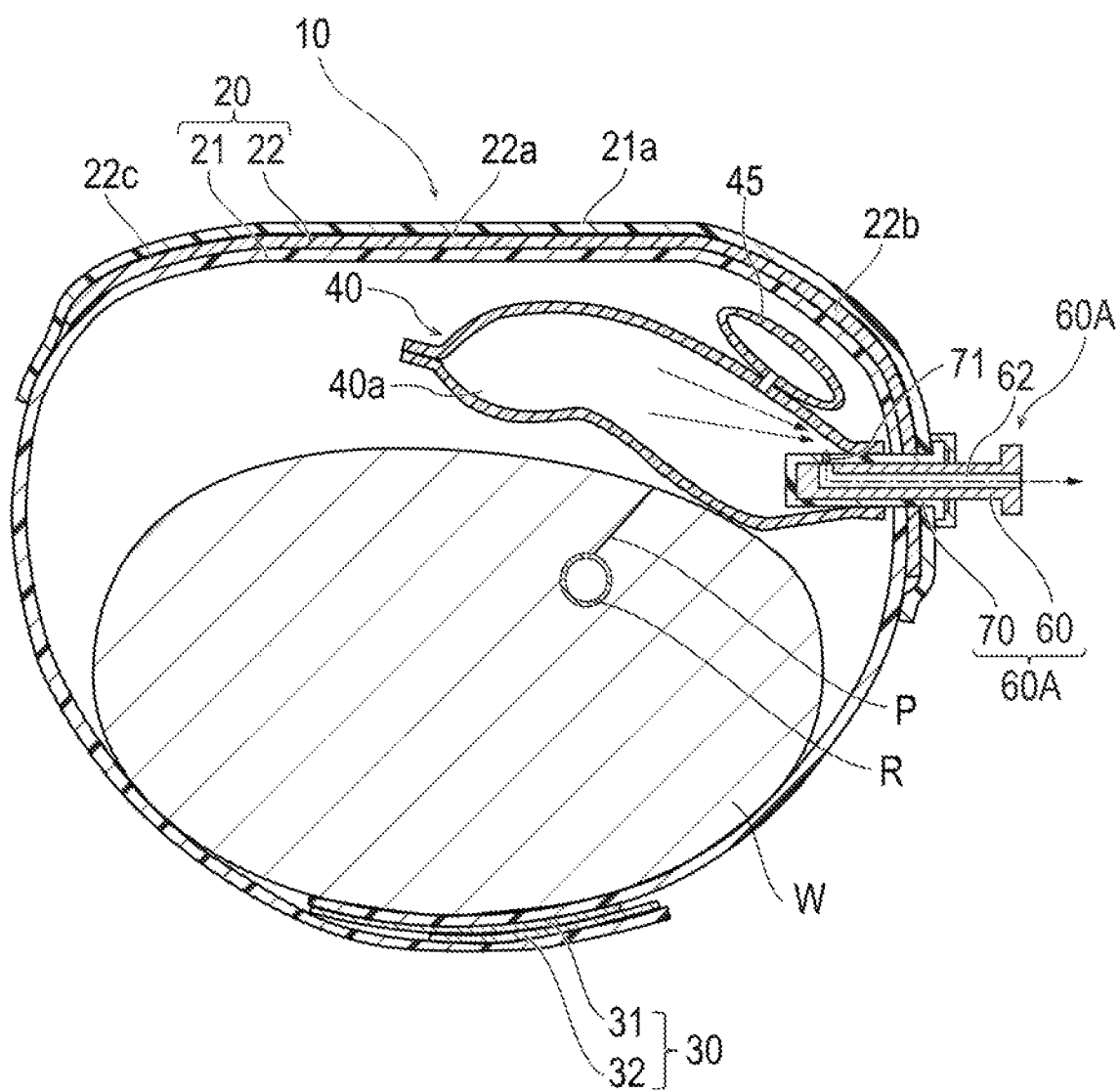
FIG. 8 is a cross-sectional view taken along 7-7 line of FIG. 6 and is a diagram illustrating an aspect when the inflatable portion is decompressed and adjusted.

A hemostatic device 10 according to the exemplary embodiment of the disclosure will be described with reference to FIG. 1 to FIG. 8. FIG. 1 to FIG. 5(B) are diagrams for description of each portion of the hemostatic device 10. FIG. 6 to FIG. 8 are diagrams for description of a use example of the hemostatic device 10.

As illustrated in FIG. 6 to FIG. 8, to insert a catheter, etc. for performing treatment/examination, etc. into a blood vessel, after withdrawing an introducer sheath indwelled in a puncture site P (corresponding to a "site where bleeding is to be stopped") formed in a radial artery R of a wrist W (corresponding to a "limb"), the hemostatic device 10 according to the exemplary embodiment is used to stop bleeding in the puncture site P.

Figure 2:
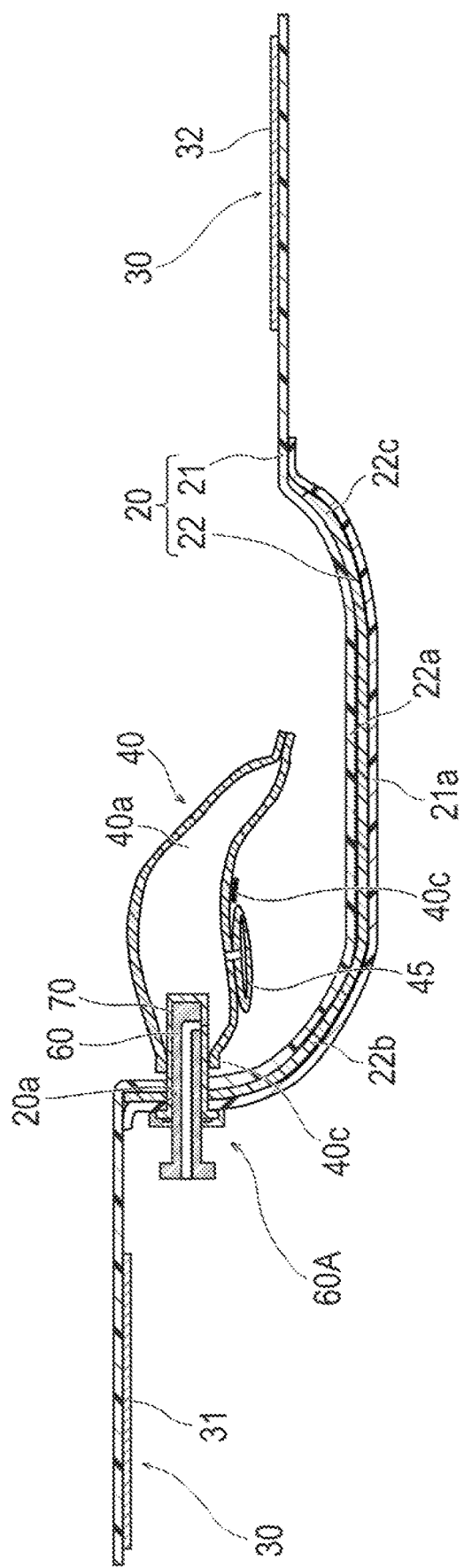
FIG. 2 is a cross-sectional view taken along 2-2 line of FIG. 1.

As illustrated in FIG. 1 and FIG. 2, the hemostatic device 10 includes a band 20 for wrapping around the wrist W, a surface fastener 30 (corresponding to "means for securing (securing member)") that secures the band 20 in a state of being wrapped around the wrist W, an inflatable portion 40 inflated by being injected with air (corresponding to "gas") to press the puncture site P, an auxiliary pressing portion 45 provided between the inflatable portion 40 and the band 20, a marker 40c for positioning the inflatable portion 40 at the puncture site P, an injection part 50 capable of injecting air into the inflatable portion 40, and a tube body 60 that connects an inflatable space (lumen) 40a of the inflatable portion 40 to an outside (outside of the inflatable space 40a).

In the disclosure herein, when the band 20 is wrapped around the wrist W, a surface (mounting surface) on a side facing a body surface of the wrist W is referred to as an "inner surface" (corresponding to a "first surface"), and a surface on an opposite side is referred to as an "outer surface" (corresponding to a "second surface").

The band 20 includes a belt 21 made of a belt-shaped member having flexibility, and a support plate 22 having a higher hardness than that of the belt 21.

As illustrated in FIG. 6 and FIG. 7, the belt 21 is wrapped around an outer periphery of the wrist W substantially once. As illustrated in FIG. 2, a support plate holding portion 21a that holds the support plate 22 is formed at a central portion of the belt 21. The support plate holding portion 21a is doubled by separate belt-shaped members joined to an outer surface side (or inner surface side) using a method such as welding (heat-welding, high-frequency welding, ultrasound welding, etc.) or adhesion (adhesion by an adhesive or a solvent) and holds the support plate 22 inserted into a gap therebetween.

A male side (or a female side) 31 of the surface fastener 30 is disposed on an outer surface side of a portion of the belt 21 near a left end as illustrated in FIG. 1, and a female side (or a male side) 32 of the surface fastener 30 is disposed on an inner surface side of a portion of the belt 21 near a right end as illustrated in FIG. 1. For example, the surface fastener 30 is a hook and loop fastener known as a general product such as VELCRO (registered trademark) or Magic tape (registered trademark) in Japan. As illustrated in FIG. 7, the belt 21 is wrapped around the wrist W, and the male side 31 and the female side 32 are joined together, thereby mounting the band 20 on the wrist W. Note that means for securing the band 20 to the wrist W in a wrapped state is not limited to the surface fastener 30. For example, it is possible to use a securing member such as a snap, a button, a clip, or a frame member passing the end portion of the belt 21.

A constituent material of the belt 21 is not particularly limited as long as the material has flexibility. Examples of such a material include polyvinyl chloride, polyolefins such as polyethylene, polypropylene, polybutadiene and ethylene-vinyl acetate copolymers (EVA), polyesters such as polyethylene terephthalate (PET) and polybutylene terephthalate (PBT), polyvinylidene chloride, silicone, polyurethane, various thermoplastic elastomers such as polyamide elastomers, polyurethane elastomers and polyester elastomers, and an arbitrary combination of the above (blend resin, polymer alloy, laminate, etc.).

In addition, at least a part of the belt 21 overlapping with the inflatable portion 40 is preferably substantially transparent. However, the part may not be transparent, and may be translucent or colored transparent. In this way, the puncture site P may be visually recognized from the outer surface side, and the marker 40c described below may be easily positioned at the puncture site P.

As illustrated in FIG. 2, the support plate 22 is held in the belt 21 by being inserted into the doubly formed support plate holding portion 21a of the belt 21. At least a part of the support plate 22 has a plate shape curved toward the inner surface side (mounting surface side). The support plate 22 is made of a harder material than that of the belt 21 and is designed to maintain a substantially constant shape. However, a method of disposing the support plate 22 on the belt 21 is not limited to an illustrated configuration, and it is possible to include joining the support plate 22 to the inner surface or the outer surface of the band 20 using an appropriate method such as welding or adhesion. Similarly, another acceptable configuration is a configuration in which the belt 21 is connected to both end portions of the support plate 22. For this reason, it is not always necessary that the entire support plate 22 overlaps the belt 21.

The support plate 22 has a shape elongated in a longitudinal direction of the belt 21. A central portion 22a in a longitudinal direction of the support plate 22 is formed in a flat plate shape with little curvature. A first curved portion 22b (left side of FIG. 2) and a second curved portion 22c (right side of FIG. 2) curved toward an inner circumference side and along the longitudinal direction of the belt 21 (circumferential direction of the wrist W) are formed on both sides of the central portion 22a, respectively.

A constituent material of the support plate 22 include acrylic resins, polyvinyl chloride (particularly rigid polyvinyl chloride), polyolefins such as polyethylene, polypropylene and polybutadiene, polystyrene, poly(4-methyl pentene-1), polycarbonates, ABS resins, polymethyl methacrylate (PMMA), polyacetals, polyarylates, polyacrylonitriles, polyvinylidene fluorides, ionomers, acrylonitrile-butadiene-styrene copolymers, polyesters such as polyethylene terephthalate (PET) and polybutylene terephthalate (PBT), butadiene-styrene copolymers, aromatic or aliphatic polyamides, and fluorocarbon resins such as polytetrafluoroethylene.

It is preferable that a part of the support plate 22 overlapping the inflatable portion 40 is substantially transparent similar to the belt 21. However, the part may not be transparent, and may be translucent or colored transparent. In this way, the puncture site P may be reliably visually recognized from the outer surface side, and the marker 40c described below may be easily positioned at the puncture site P. Note that the support plate 22 may not have a non-curved portion as the central portion 22a, and may be curved over an entire length thereof.

The inflatable portion 40 has a function of inflating by being injected with air to apply a pressing force to the puncture site P. In the exemplary embodiment, as illustrated in FIG. 1 and FIG. 2, the inflatable portion 40 is formed of a bag-shaped member obtained by superimposing two substantially rectangular sheets and bonding or welding a circumference thereof. In this way, the inflatable space 40a is formed between the two sheets. Note that a configuration of the inflatable portion 40 is not particularly limited as long as the inflatable portion 40 can be inflated by being injected with air. For example, the inflatable portion 40 may be formed of a bag-shaped member obtained by folding one sheet and bonding or welding edge portions, or formed of a balloon-shaped member not having an edge portion. In addition, an external shape of the inflatable portion 40 is not particularly limited. For example, the inflatable portion 40 may have an external shape such as a circle, an ellipse, or a polygon in plan view in a non-inflated state.

As illustrated in FIG. 2, the inflatable portion 40 is disposed to overlap a vicinity of a portion between the first curved portion 22b and the central portion 22a of the support plate 22. For this reason, as illustrated in FIG. 7, when the inflatable portion 40 is inflated, inflation of the inflatable portion 40 in a direction away from the body surface of the wrist W is suppressed by the belt 21 and the support plate 22, and a pressing force of the inflatable portion 40 is concentrated on the wrist W side. Thus, it is possible to suitably press the puncture site P.

The inflatable portion 40 has a connecting portion 40b connected to the cover portion 70 disposed on the tube body 60. The inflatable portion 40 is connected to the cover portion 70 through the connecting portion 40b in a state in which a part of the cover portion 70 is inserted into the inflatable space 40a. In addition, the cover portion 70 is connected to the band 20 in a state of penetrating a through-hole 20a formed in the band 20. A method of connecting the inflatable portion 40 to the cover portion 70 and a method of connecting the cover portion 70 to the band 20 are not particularly limited. For example, it is possible to adopt a method such as welding or adhesion using an adhesive. Also, the inflatable portion 40 may be directly connected to the belt 21 of the band 20.

A constituent material of the inflatable portion 40 is not particularly limited as long as the material has flexibility. For example, it is possible to use the same material as the constituent material of the band 20 described above.

It is preferable that the inflatable portion 40 is substantially transparent. However, the inflatable portion 40 may not be transparent, and may be translucent or colored transparent. In this way, it is possible to visually recognize the puncture site P from the outer surface side, and to easily position the marker 40c described below at the puncture site P.

As indicated by an arrow in FIG. 7, the auxiliary pressing portion 45 has a function of pressing the inflatable portion 40 to adjust a direction of a pressing force applied to the puncture site P by the inflatable portion 40.

Similar to the inflatable portion 40, the auxiliary pressing portion 45 is formed of a bag-shaped member. Note that for example, the auxiliary pressing portion 45 may be made of a sponge-like substance, an elastic material, an aggregate of fibers such as cotton, a combination thereof, etc.

The auxiliary pressing portion 45 is attached to the inflatable portion 40 such that an internal space thereof communicates with the inflatable space 40a of the inflatable portion 40. For this reason, when air is injected into the inflatable portion 40, the auxiliary pressing portion 45 is also inflated.

As illustrated in FIG. 2, the marker 40c is provided at an approximate center of the inflatable portion 40 on a side facing the band 20. When such a marker 40c is provided on the inflatable portion 40, the inflatable portion 40 can be easily positioned with respect to the puncture site P, and thus position shift of the inflatable portion 40 is suppressed. Note that the marker 40c may be provided on a side of the inflatable portion 40 facing the wrist W. In this instance, it is preferable that the marker 40c is provided on the inner surface of the inflatable portion 40 so as not to directly come into contact with the puncture site P. Note that a position at which the marker 40c is provided is not particularly limited as long as the inflatable portion 40 can be positioned at the puncture site P. For example, the marker 40c may be provided on the belt 21 or the support plate 22 as long as the inflatable portion 40 can be positioned at the puncture site P.

A shape of the marker 40c is not particularly limited, and examples thereof include a circle, a triangle, a quadrangle, etc. In present embodiment, the shape corresponds to the quadrangle.

A size of the marker 40c is not particularly limited. For example, when the shape of the marker 40c corresponds to the quadrangle, it is preferable that a length of one side thereof is in a range of 1 to 4 mm. When the length of the one side is 5 mm or more, the size of the marker 40c increases with respect to a size of the puncture site P, and thus it is difficult to position a central portion of the inflatable portion 40 in the puncture site P.

A material of the marker 40c is not particularly limited. Examples thereof include an oily coloring agent such as ink, a resin kneaded with a pigment, etc.

A color of the marker 40c is not particularly limited when the color allows the inflatable portion 40 to be positioned at the puncture site P. However, a green-based color is preferable. When the green-based color is adopted, it is easy to visually recognize the marker 40c on blood or skin, and thus the inflatable portion 40 is more easily positioned at the puncture site P.

In addition, the marker 40c is preferably translucent or colored transparent. In this way, the puncture site P may be visually recognized from the outer surface side of the marker 40c.

A method of providing the marker 40c on the inflatable portion 40 is not particularly limited. Examples thereof include a process of printing the marker 40c on the inflatable portion 40, a method of welding the marker 40c to the inflatable portion 40, a method of applying an adhesive to one surface of the marker 40c to paste the marker 40c to the inflatable portion 40, etc.

The injection part 50 is a part for injecting air into the inflatable portion 40 and is connected to the inflatable portion 40 as illustrated in FIG. 1.

The injection part 50 includes a tube 51 having flexibility, a proximal portion of the tube being connected to the inflatable portion 40 and a lumen of the tube communicates with the inflatable space 40a of the inflatable portion 40, a bag body 52 disposed at a distal portion of the tube 51 to communicate with a lumen of the tube 51, and a tube-shaped connector 53 incorporating a check valve (not illustrated) connected to the bag body 52.

At the time of inflating (expanding) the inflatable portion 40, a tip of a syringe (not illustrated) is inserted into the connector 53 to open the check valve, and a plunger of the syringe is pushed to inject air in the syringe into the inflatable portion 40 through the injection part 50. When the inflatable portion 40 inflates, the bag body 52 communicating with the inflatable portion 40 through the tube 51 also inflates, and it is possible to visually confirm that the inflatable portion 40 can be pressed without leakage of air. When the tip of the syringe is withdrawn from the connector 53 after air is injected into the inflatable portion 40, the check valve incorporated in the connector 53 is closed to prevent leakage of air.

Next, the tube body 60 and the cover portion 70 will be described with reference to respective drawings. Note that FIG. 3 illustrates a schematic perspective view of the tube body 60 and the cover portion 70, and each of FIG. 4(A)-FIG. 5(B) illustrates a simplified plan view and cross-sectional view of the tube body 60 and the cover portion 70.

As illustrated in FIG. 2, the tube body 60 communicates between the inflatable space 40a in the inflatable portion 40 and the outside. In addition, as illustrated in FIG. 3 and FIG. 4(A), the tube body 60 has a hole portion 61 opening in the inflatable portion 40, a lumen 62 through which air can flow, a proximal end opening 63 disposed outside the inflatable portion 40, a first member 64 included in a lock mechanism, and a grip portion 65 that can be gripped by fingers, etc.

Figure 3:
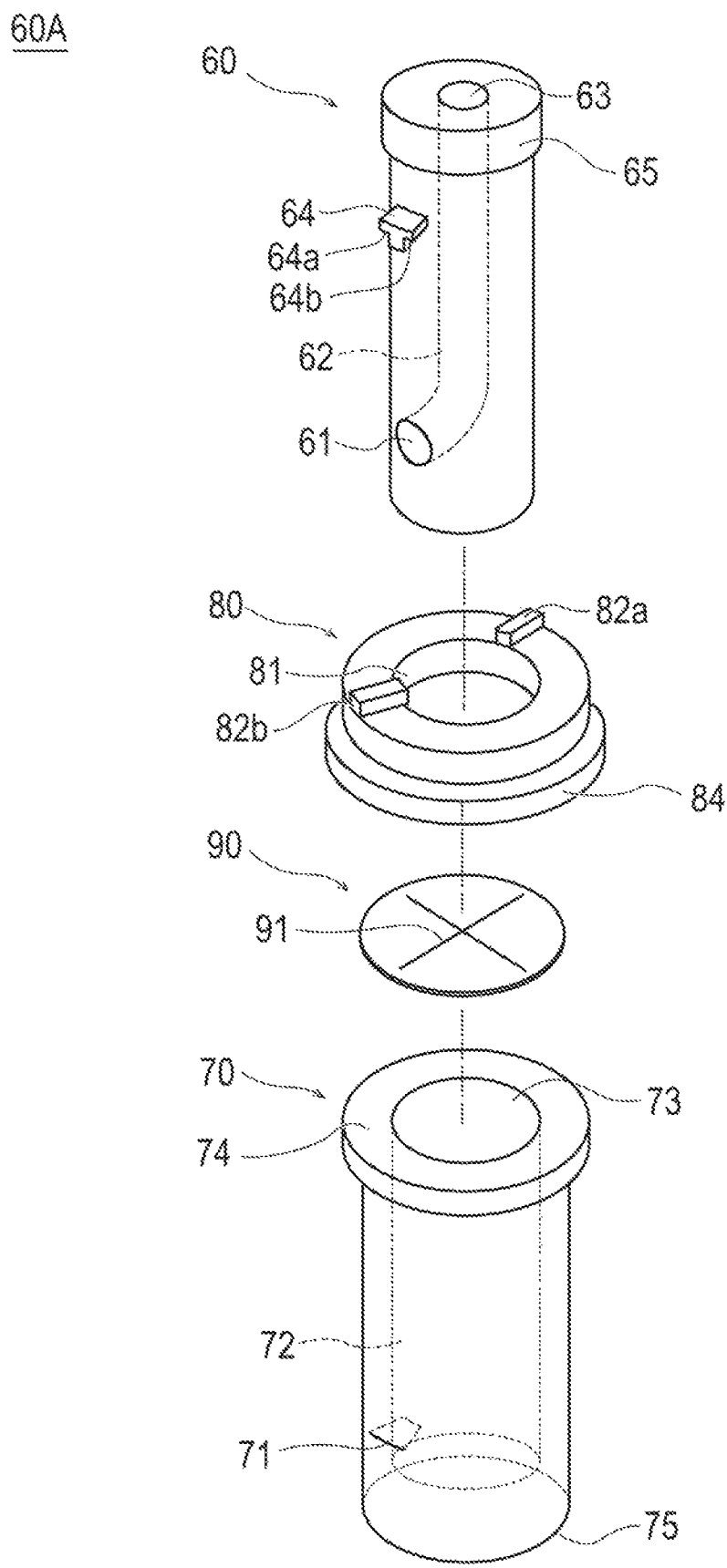
FIG. 3 is a schematic perspective view of a tube body and a cover portion included in the hemostatic device according to the exemplary embodiment of the disclosure.
Figure 4B:
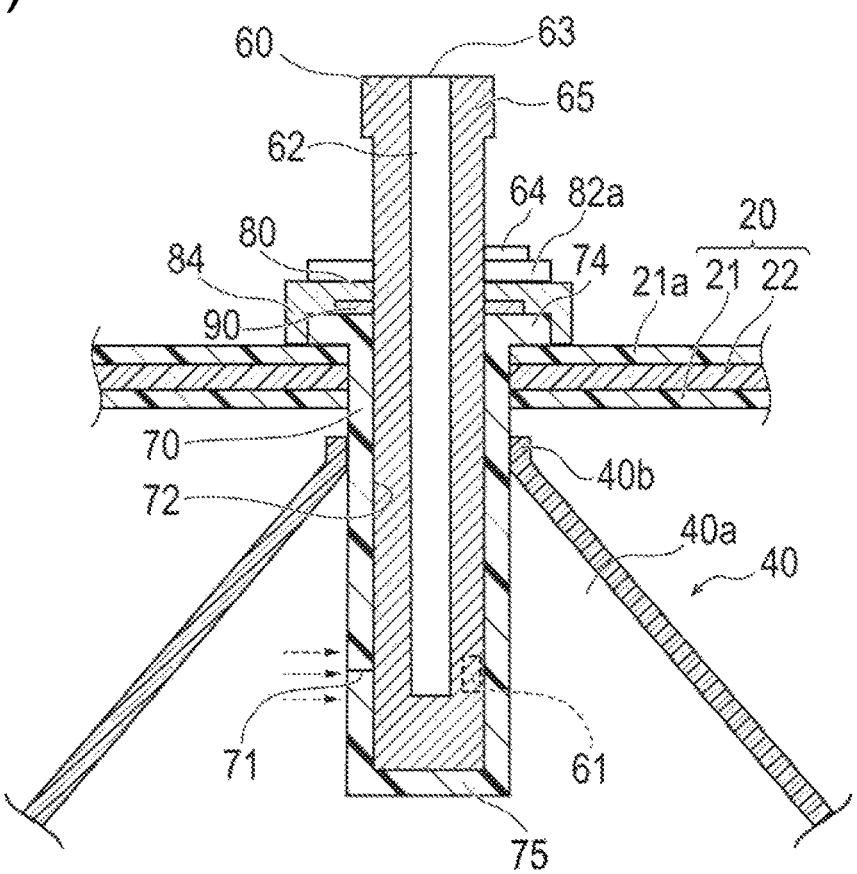
FIG. 4(B) is a cross-sectional view taken along 4B-4B line illustrated in FIG. 4(A).

As illustrated in FIG. 3 and FIG. 4(B), the cover portion 70 is disposed to cover the tube body 60 in the inflatable portion 40. In addition, the cover portion 70 is disposed to cover the hole portion 61 of the tube body 60.

The cover portion 70 has a communication portion 71 positioned to overlap the hole portion 61 of the tube body 60 so that the hole portion 61 and the inflatable portion 40 can communicate with each other, a lumen 72 into which the tube body 60 is inserted, a proximal end opening 73 provided at a proximal side, a flange portion 74 disposed around the proximal end opening 73, and a bottom face part 75 covering a distal portion of the tube body 60.

Note that a specific shape of the cover portion 70 is not limited as long as the cover portion 70 has the communication portion 71 that can be positioned to overlap the hole portion 61 of the tube body 60. For example, the cover portion 70 may be configured in a shape in which the bottom face part 75 covering the distal portion of the tube body 60 is not provided.

As illustrated in FIG. 3 and FIG. 4(B), a distal side (lower side of FIG. 4(B)) of the tube body 60 is inserted into the lumen 72 of the cover portion 70. The tube body 60 is configured to be rotatable with respect to the cover portion 70 when inserted into the lumen 72 of the cover portion 70. The distal side of the tube body 60 inserted into the lumen of the cover portion 70 is formed in a substantially cylindrical shape. The lumen 72 of the cover portion 70 is formed in a substantially cylindrical shape so that the tube body 60 can be inserted.

The lumen 62 of the tube body 60 is formed along an extending direction (axial direction) of the tube body 60. The hole portion 61 is formed at the distal side (lower side of FIG. 3) of the tube body 60, and opens toward the outer surface of the tube body 60 so as to be substantially orthogonal to the lumen 62 of the tube body 60.

It is preferable that an inner diameter of the cover portion 70 (diameter of the lumen 72) is the same as an outer diameter of the tube body 60 or smaller than the outer diameter of the tube body 60 so that the tube body 60 is rotatable and an excessive clearance is not formed between the outer surface of the tube body 60 and an outer surface of the cover portion 70.

A rotation range of the tube body 60 (a distance in which rotation is allowed in a circumferential direction with respect to the cover portion 70) may be arbitrarily set and is not particularly limited. For example, as illustrated in FIG. 4(A) and FIG. 4(B), the rotation range of the tube body 60 may be formed to be able to maintain a distance between the hole portion 61 and the communication portion 71 so that the communication portion 71 does not open in a state in which the hole portion 61 of the tube body 60 and the communication portion 71 of the cover portion 70 do not overlap each other.

In addition, as illustrated in FIG. 3 and FIG. 4(B), a valve body 90 is disposed on the flange portion 74 of the tube body 60. The valve body 90 has a slit 91 through which the tube body 60 can be inserted. The valve body 90 prevents air from leaking from between the tube body 60 and the cover portion 70. Note that shapes, structures, etc. of the valve body 90 and the slit 91 are not particularly limited as long as the tube body 60 can be inserted and leakage of air from the inflatable portion 40 can be prevented.

A lid member (support body) 80 is disposed on a proximal side of the cover portion 70. The lid member 80 has an opening 81 through which the tube body 60 is inserted, second members 82a and 82b that restrict rotation of the tube body 60 in cooperation with the first member 64 formed on the tube body 60, and a predetermined flange portion 84.

As illustrated in FIG. 4(B), the valve body 90 is interposed between the flange portion 74 of the cover portion 70 and the lid member 80. In addition, the band 20 and the flange portion 84 of the lid member 80 are secured to each other. As illustrated in FIG. 3, the tube body 60 is inserted into the lumen 72 of the cover portion 70 by being inserted through the opening 81 of the lid member 80, the slit 91 of the valve body 90, and the proximal end opening 73 of the cover portion 70. In the exemplary embodiment, the tube body 60, the cover portion 70, the lid member 80, and the valve body 90 are included in a decompression adjustment mechanism 60A that enables an operation of discharging air from the inflatable portion 40 (see FIG. 3).

It is preferable that a constituent material of the tube body 60 is a material having a higher hardness than that of the cover portion 70. Examples of such a material include a known metallic material, a plastic material, etc.

A constituent material of the cover portion 70 preferably corresponds to an elastic member. Examples of such a material include an elastomer material such as butyl rubber, polysulfide rubber, epichlorohydrin rubber, high nitrile rubber, fluororubber, or silicone rubber, various thermoplastic elastomer materials, etc.

A constituent material of the valve body 90 is not particularly limited, and examples thereof include silicone rubber, latex rubber, butyl rubber and isoprene rubber which are elastic members.

A constituent material of the lid member 80 is not particularly limited. For example, it is possible to use the same material as the constituent material of the band 20 described above. The flange portion 84 of the lid member 80 is secured to the band 20 or the flange portion 74 of the cover portion 70. For example, the flange portion 84 of the lid member 80 is secured to the band 20 or the flange portion 74 of the cover portion 70 using a method such as welding or adhesion. Note that the valve body 90 is disposed between the lid member 80 and the flange portion 74 of the cover portion 70 by being interposed between the lid member 80 and the flange portion 74 of the cover portion 70.

In the exemplary embodiment, the communication portion 71 of the cover portion 70 is formed as a slit (cut) penetrating the cover portion 70 in a thickness direction. The slit is formed at a position overlapping the hole portion 61 in a cross section perpendicular to an axial center of the tube body 60 (cross section illustrated in FIG. 4(B)). In addition, one slit is formed in the cover portion 70 in a shape extending in a direction orthogonal to an extending direction (axial direction) of the cover portion 70.

As described above, by way of example, the communication portion 71 may be formed as the slit. However, as described below, the communication portion 71 may be configured such that it is possible to switch between communication between the inflatable space 40*a* of the inflatable portion 40 and the lumen 62 of the tube body 60 and blocking of the communication state, and it is not limited to a form of the slit. For example, the communication portion 71 may be formed as a small hole having the same function as that of the slit. In addition, for example, the communication portion 71 may be formed as a plurality of slits, formed as a slit having a shape extending in a direction inclined with respect to the extending direction of the cover portion 70, or formed as a plurality of slits intersecting and overlapping each other. A specific shape, structure, arrangement, etc. are not particularly limited. In addition, in a case in which the communication portion 71 is formed as the small hole, a specific shape, size, structure, arrangement, etc. are not similarly particularly limited, and it is possible to adopt the above exemplified configuration, etc.

In addition, in the exemplary embodiment, the hole portion 61 included in the tube body 60 is formed in a circular shape in plan view. However, the shape of the hole portion 61 is not particularly limited as long as air can flow, and may correspond to, for example, a rectangular shape, an elliptical shape, a trapezoidal shape, another polygonal shape, etc. in plan view.

Note that when the communication portion 71 of the cover portion 70 is formed as a slit, it is preferable that a length (length along a direction intersecting an axial direction of the cover portion 70) of the slit is longer than a diameter of the hole portion 61. According to such a configuration, when positions of the hole portion 61 and the communication portion 71 are superimposed with each other, the slit is more easily opened by an internal pressure of the inflatable portion 40. For this reason, the hemostatic device 10 can more appropriately control a discharged amount of air.

The first member 64 of the tube body 60 and the respective second members 82*a* and 82*b* of the lid member 80 are included in a lock mechanism that restricts relative movement of the tube body 60 with respect to the cover portion 70.

As illustrated in FIG. 3, the first member 64 has two recesses corresponding to a first recess 64*a* and a second recess 64*b*. As illustrated in FIG. 4(A), the first recess 64*a* is configured to be able to engage (secure) the second member 82*a* of the lid member 80. In addition, as illustrated in FIG. 5(A), the second recess 64*b* is configured to be able to engage (secure) the second member 82*b* of the lid member 80. Rotation of the tube body 60 is thus restricted by engagement of the first recess 64*a* and the second member 82*a* and engagement of the second recess 64*b* and the second member 82*b* secured to each other. In other words, the first and second recesses act as rotation stop limits when engaged by the first and second members.

As described above, the lock mechanism restricts rotation of the tube body 60 by the first recess 64*a* and the second member 82*a* engaging each other at a position at which the hole portion 61 and the communication portion 71 do not overlap each other, and the second recess 64*b* and the second member 82*b* engaging each other at a position at which the hole portion 61 and the communication portion 71 overlap each other. For this reason, it is possible to easily check a situation in which the hole portion 61 is disposed at a position at which the inflatable portion 40 is decompressed or the hole portion 61 is disposed at a position at which the inflatable portion 40 is decompressed by a feeling of a finger touching the grip portion 65 of the tube body 60 at the time of operating the tube body 60.

Note that a configuration of the lock mechanism is not particularly limited as long as rotation of the tube body 60 can be restricted. The lock mechanism is not limited to a structure in which movement of the tube body 60 is restricted by mechanical connection (engagement contact) between members. For example, it is possible to adopt a structure in which rotation of the tube body 60 is restricted by a magnetic force, etc. In addition, for example, the lock mechanism may not be configured to restrict rotation of the tube body 60 at the position at which the hole portion 61 and the communication portion 71 do not overlap each other and at the position at which the hole portion 61 and the communication portion 71 overlap each other, but may be configured to restrict rotation at only one of the two positions. However, to prevent the inflatable portion 40 from being inadvertently decompressed, it is preferable that the lock mechanism is configured to restrict rotation of the tube body 60 at least at the position at which the hole portion 61 and the communication portion 71 do not overlap each other.

Next, a description will be given of a procedure example of a decompression operation of the inflatable portion 40 by the decompression adjustment mechanism 60A with reference to FIG. 4(A)-FIG. 5(B).

FIG. 4(A) and FIG. 4(B) illustrate a state in which air is injected into the inflatable space 40*a* of the inflatable portion 40. In this state, the hole portion 61 of the tube body 60 is not disposed at a position overlapping the communication portion 71 of the cover portion 70. Since a pressure in the inflatable portion 40 is larger than a pressure in the lumen 62 of the tube body 60, the communication portion 71 maintains a closed state due to a pressure difference.

Figure 5B:
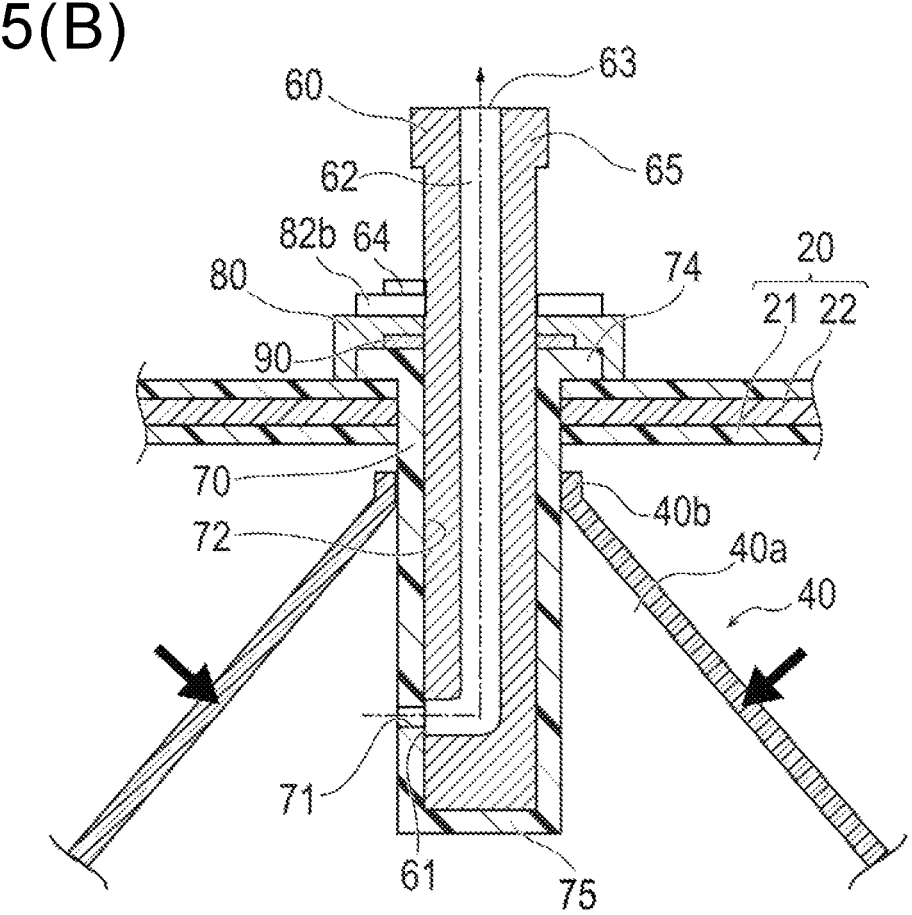
FIG. 5(B) is a cross-sectional view taken along 5B-5B line illustrated in FIG. 5(A).

As illustrated in FIG. 5(A) and FIG. 5(B), when the tube body 60 is rotated to overlap positions of the hole portion 61 and the communication portion 71, a slit forming the communication portion 71 is pressed toward the hole portion 61 side by the internal pressure of the inflatable portion 40 to open the slit. In this way, the communication portion 71 allows communication between the lumen 62 of the tube body 60 and the inflatable space 40*a* of the inflatable portion 40. Air in the inflatable space 40*a* of the inflatable portion 40 is discharged to the outside via the lumen 62 of the tube body 60. Since an amount of air discharged from the inflatable portion 40 when the position of the hole portion 61 and the position of the communication portion 71 overlap each other is controlled based on a shape and a size (dimension) of the slit forming the communication portion 71, it is possible to quantitatively control the amount of discharged air, and to appropriately discharge a desired amount of air.

When the decompression operation of the inflatable portion 40 is completed, the tube body 60 is rotated to adjust a positional relation between the hole portion 61 and the communication portion 71 so that the positions thereof do not overlap each other. In this way, the hemostatic device 10 may perform decompression adjustment of the inflatable portion 40 by a simple operation of rotating the tube body 60. In addition, in the hemostatic device 10, a mechanism (the hole portion 61 and the communication portion 71) for switching between communication between the inflatable space 40*a* of the inflatable portion 40 and the lumen 62 of the tube body 60 and blocking of the communication state is disposed inside the inflatable portion 40. Thus, it is possible to prevent a doctor, a patient, etc. from inadvertently touching the mechanism or the mechanism from being clogged with minute foreign matter, thus enhancing safety of a hemostatic treatment.

Next, a description will be given of a method of using the hemostatic device 10 according to the exemplary embodiment.

Before the hemostatic device 10 is mounted on the wrist W, as illustrated in FIG. 2, the inflatable portion 40 is in a state of not being inflated. As illustrated in FIG. 6, when the radial artery R of the right hand wrist W is punctured, the puncture site P is at a position biased to a thumb side. Normally, the introducer sheath is indwelled in the puncture site P. The band 20 is wrapped around the wrist W in which the introducer sheath is indwelled, the inflatable portion 40 and the band 20 are positioned such that the marker 40*c* provided on the inflatable portion 40 overlaps the puncture site P, and the male side 31 and the female side 32 of the surface fastener 30 are brought into contact with each other and joined to each other, thereby mounting the band 20 on the wrist W.

In this instance, the hemostatic device 10 is mounted on the wrist W such that the injection part 50 faces the downstream side (palm side) of a blood flow of the radial artery R. In this way, the injection part 50 may be operated without interfering with manipulation on the upstream side of the wrist or a device (for example, a sphygmomanometer) located on the upstream side. In addition, when the hemostatic device 10 is mounted on the right hand wrist W such that the injection part 50 faces the downstream side, the inflatable portion 40 is located on the radial artery R biased to the thumb side of the wrist W. Note that in the case of the artery, the upstream side of the blood vessel refers to a direction of the blood vessel approaching a heart. In addition, the downstream side of the blood vessel refers to a direction of the blood vessel away from the heart.

Note that the hemostatic device 10 may be used for puncturing the radial artery of the left hand wrist. In this case, the injection part 50 is mounted on the left hand wrist to face the upstream side of the blood flow of the radial artery.

After the hemostatic device 10 is mounted on the wrist W, the syringe (not illustrated) is connected to the connector 53 of the injection part 50, air is injected into the inflatable portion 40 as described above, and the inflatable portion 40 is inflated as illustrated in FIG. 7.

A degree of inflation of the inflatable portion 40, that is, a pressing force acting on the puncture site P may be easily adjusted depending on the case according to an injection amount of air at this time. For example, when air is excessively injected into the inflatable portion 40, and thus the inflatable portion 40 is excessively inflated, excessively injected air may be discharged from the inside of the inflatable portion 40 using the syringe, or air may be discharged using the decompression adjustment mechanism 60A.

After the inflatable portion 40 is inflated, the syringe is detached from the connector 53. Then, the introducer sheath is withdrawn from the puncture site P.

It is possible to adjust the amount of air to the inflatable portion 40 and the auxiliary pressing portion 45 and adjust a pressing force applied to the puncture site P by the inflatable portion 40 by operating the decompression adjustment mechanism 60A according to a progressing state of hemostasis and an elapsed time after withdrawing the introducer sheath (see FIG. 8). For example, when the inflated inflatable portion 40 continues to press the puncture site P and a surrounding blood vessel or nerve for a long time, there is the case of causing numbness or pain or occluding the blood vessel. In order to prevent vascular occlusion, etc., the pressing force acting on the puncture site P may be reduced over time by performing a decompression operation of discharging air in the inflatable portion 40 over time after inflation of the inflatable portion 40 to gradually decrease the internal pressure of the inflatable portion 40. Since the decompression adjustment in the hemostatic device 10 can be performed by the decompression adjustment mechanism 60A, the doctor or a nurse may eliminate the need to carry the dedicated instrument (syringe, etc.) for performing the decompression adjustment.

Note that when hemostasis is insufficiently performed after inflation of the inflatable portion 40, air may be injected into the inflatable portion 40 to raise the internal pressure of the inflatable portion 40. For example, when it is desired to return the internal pressure of the inflatable portion 40 to the internal pressure at the time of injecting air into the inflatable portion 40, air discharged from the inflatable portion 40 may again be injected by a syringe.

When a predetermined time elapses, and hemostasis of the puncture site P is completed, the hemostatic device 10 is removed from the wrist W. The hemostatic device 10 is removed from the wrist W by peeling off the male side 31 and the female side 32 of the surface fastener 30.

As described above, the hemostatic device 10 according to the exemplary embodiment includes the band 20 for wrapping around the puncture site P of the wrist W, the means for securing 30 that secures the band 20 in a state of being wrapped around the wrist W, the inflatable portion 40 connected to the band 20 and inflated by being injected with air, the tube body 60 that communicates between the inflatable space 40*a* in the inflatable portion 40 and the outside, and the cover portion 70 that covers the tube body 60 in the inflatable portion 40. In addition, the tube body 60 has the hole portion 61 that opens inside the inflatable portion 40, and the cover portion 70 has the communication portion 71 disposed to cover the hole portion 61 and positioned to overlap the hole portion 61 so that the hole portion 61 and the inflatable space 40a of the inflatable portion 40 can communicate with each other. The tube body 60 is movable relative to the cover portion 70 so that the positional relationship between the communication portion 71 and the hole portion 61 can be controlled.

In the hemostatic device 10, the tube body 60 is configured to be movable relative to the cover portion 70, and it is possible to adjust the positional relationship between the hole portion 61 of the tube body 60 and the communication portion 71 of the cover portion 70. When the communication portion 71 and the hole portion 61 are adjusted to overlapping positions, the communication portion 71 allows communication between the inflatable space 40a of the inflatable portion 40 and the outside to discharge air in the inflatable portion 40 to the outside. In addition, in a state in which the positions of the communication portion 71 and the hole portion 61 do not overlap each other, the cover portion 70 seals the hole portion 61 to prevent air from being discharged from the inflatable portion 40. As described above, according to the exemplary embodiment, it is possible to provide the hemostatic device 10 capable of performing decompression adjustment of the inflatable portion 40 by a simple operation of relatively moving the tube body 60 with respect to the cover portion 70.

In addition, the tube body 60 is rotatable relative to the cover portion 70. For this reason, it is possible to perform decompression adjustment of the inflatable portion 40 by a simple operation of rotating the tube body 60.

In addition, the communication portion 71 is disposed at the same position as that of the hole portion 61 in a cross section perpendicular to the axial center of the tube body 60. For this reason, it is possible to easily perform positioning such that the positions of the hole portion 61 and the communication portion 71 overlap each other by an operation of rotating the tube body 60.

In addition, the hemostatic device 10 has the lock mechanism for restricting movement of the tube body 60 relative to the cover portion 70. For this reason, it is possible to prevent the decompression operation from being unintentionally performed by inadvertent movement of the tube body 60.

In addition, the lock mechanism includes the first member 64 disposed on the tube body 60 and the second members 82a and 82b provided on the lid member 80 disposed on the proximal side of the cover portion 70 and configured to be engaged with and separated from the first member 64. For this reason, it is possible to prevent inadvertent movement of the tube body 60 by a simple operation of securing and separating the first member 64 and the second members 82a and 82b to and from each other.

In addition, the communication portion 71 is configured as the slit that opens at the time of being aligned with the hole portion 61. For this reason, when the communication portion 71 and the hole portion 61 are adjusted to overlapping positions, the communication portion 71 can be easily opened, and air can be suitably discharged from the inflatable portion 40.

Next, modifications of the exemplary embodiment will be described. Note that in the description of each modification, the same reference symbol will be assigned to the same configuration as that of the embodiment, and a description thereof will be omitted.

Modification 1

Figure 9:
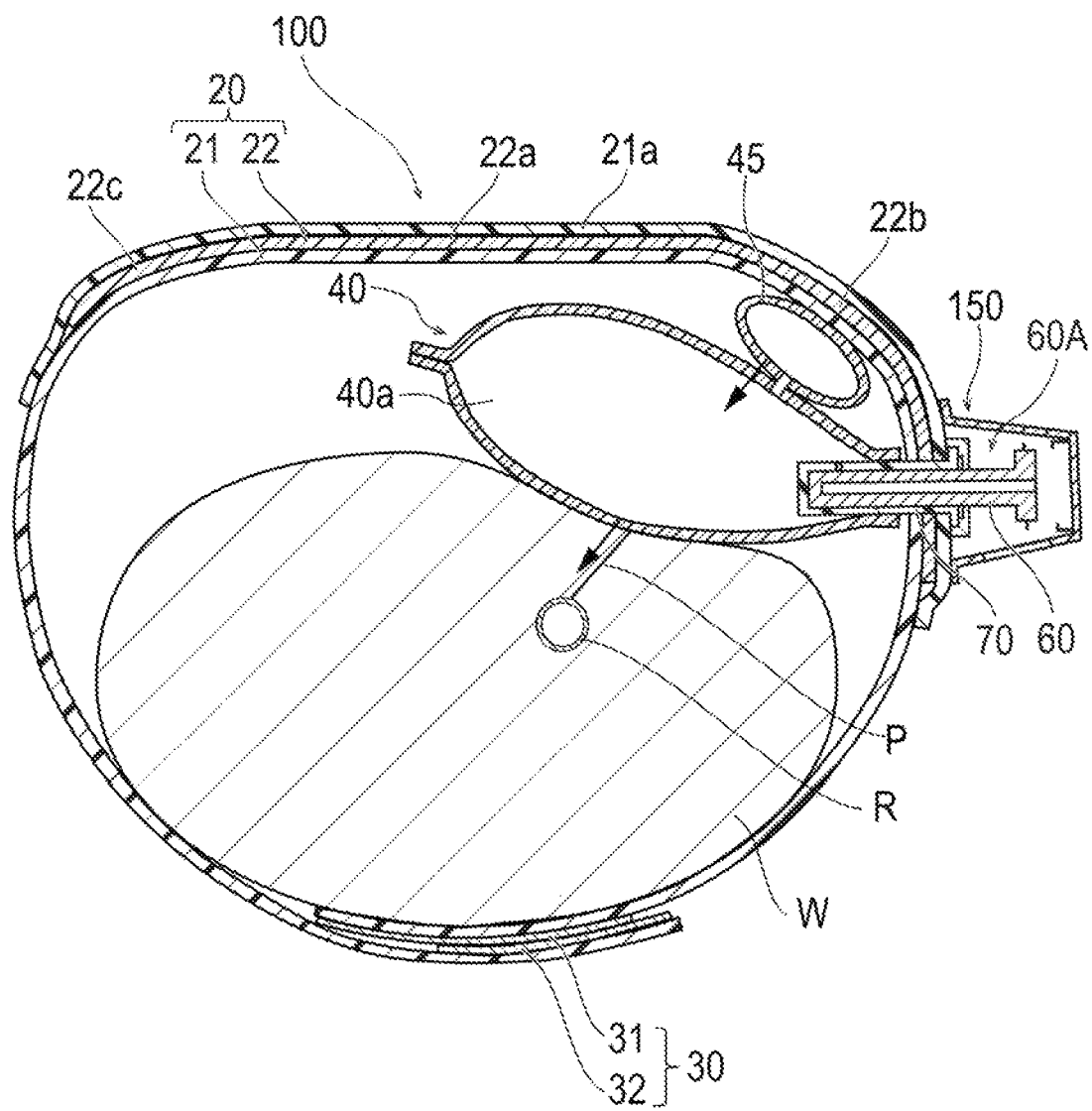
FIG. 9 is a cross-sectional view illustrating a hemostatic device according to Modification 1 of the disclosure.

FIG. 9 to FIG. 13 are diagrams for description of a hemostatic device 100 according to Modification 1. FIG. 9 illustrates a cross-sectional view of a state in which the hemostatic device 100 is mounted on the wrist W, and FIG. 10(A) to FIG. 13 illustrate cross-sectional views for description of a configuration and an operation example of each portion of the hemostatic device 100. Each of FIG. 10(A) to FIG. 12(B) illustrates a simplified plan view and cross-sectional view of the tube body 60 and the cover portion 70.

Figure 10A:
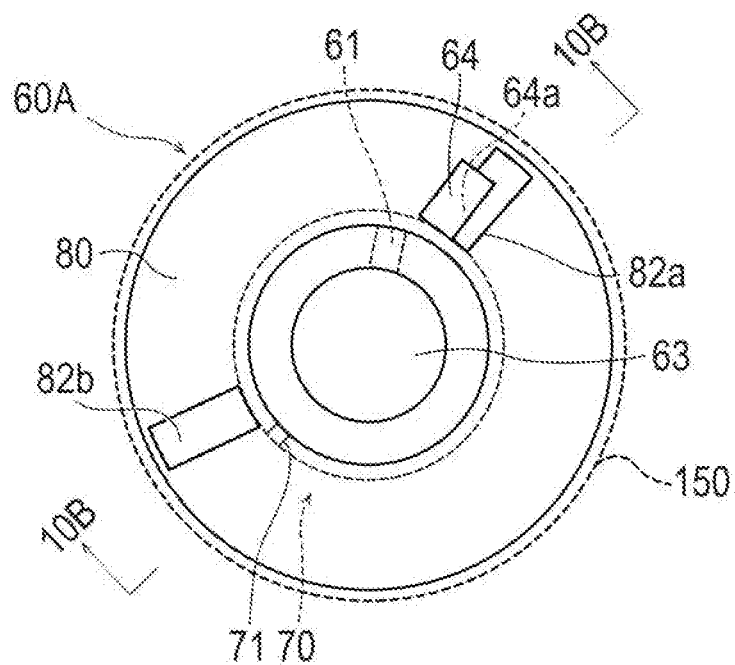
FIG. 10(A) is a plan view of a tube body and a cover portion according to Modification 1.
Figure 10B:
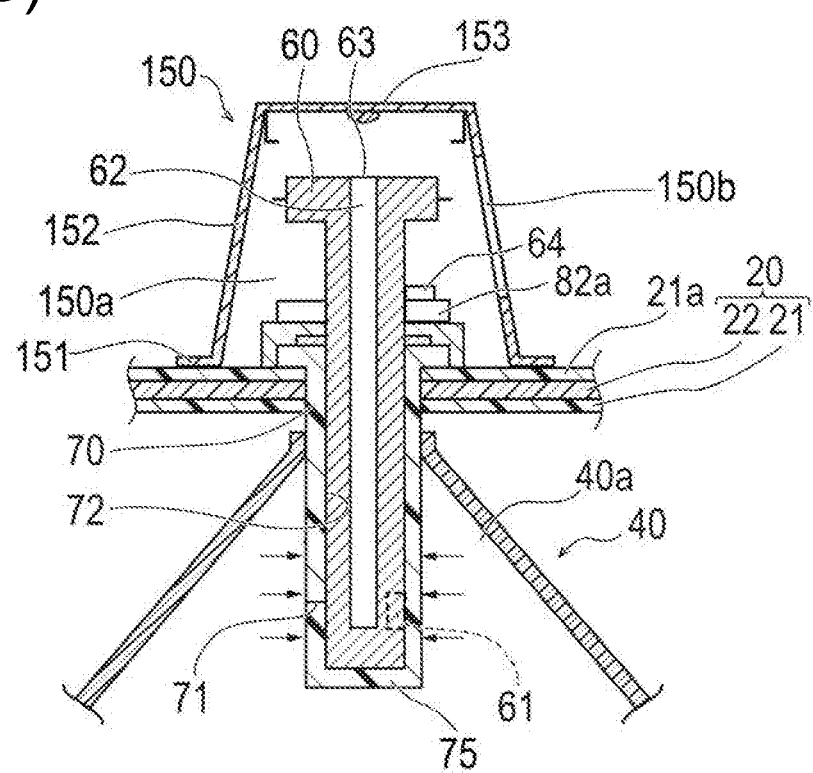
FIG. 10(B) is a cross-sectional view taken along 10B-10B line illustrated in FIG. 10(A).

As illustrated in FIG. 9 and FIG. 10(B), in the hemostatic device 100 according to Modification 1, an injection part 150 capable of injecting air into the inflatable portion 40 is provided integrally with the hemostatic device 100.

The injection part 150 has a function of injecting air into the inflatable portion 40. As illustrated in FIG. 10(B), the injection part 150 is configured by a three-dimensional (3D) member including a housing space (lumen) 150a capable of housing air. The injection part 150 is configured to be elastically transformable, and injects air into the inflatable portion 40 by being elastically transformed.

The injection part 150 is provided to surround the proximal side (upper side of FIG. 10(B)) of the tube body 60 on the outer surface side of the band 20. The lumen 62 of the tube body 60 communicates with the housing space 150a of the injection part 150 via the proximal end opening 63. The tube body 60 connects the inflatable space 40a of the inflatable portion 40 and the housing space 150a of the injection part 150 to each other. As described below, when air is injected into the inflatable portion 40 from the injection part 150, the communication portion 71 of the cover portion 70 allows communication between the inflatable space 40a and the housing space 150a by virtue of the air discharged from the hole portion 61 of the tube body 60 (see FIG. 11(B)).

The injection part 150 includes a bottom face part 151 disposed on the outer surface side of the band 20, a vertical wall part 152 projecting from the bottom face part 151 to a side at which the band 20 is not provided, and an upper face part 153 which is continued from the vertical wall part 152 and faces the bottom face part 151. A hole portion 150b communicating between an inside and an outside of the housing space 150a is formed in the vertical wall part 152.

The housing space 150a corresponds to a space surrounded by the bottom face part 151, the vertical wall part 152, and the upper face part 153. Note that in the embodiment of Modification 1, the injection part 150 is formed to have a columnar external shape. However, the external shape of the injection part 150 is not particularly limited. For example, the external shape of the injection part 150 may correspond to a polygonal prism such as a quadrangular prism, a sphere having no distinction between the bottom face part, the vertical wall part, and the upper face part, etc.

The volume of the housing space 150a of the injection part 150 is preferably about ¼ to ⅓ of the volume of the inflatable space 40a of the inflatable portion 40. In this way, the injection part 150 is formed to an appropriate size to prevent the injection part 150 from hindering manipulation, etc. performed around the hemostatic device 10, and it is possible to reduce the number of times of performing an injection operation of injecting air into the inflatable portion 40 described below.

The injection part 150 is disposed on the outer surface side of the band 20. For this reason, when compared to a case in which the injection part 150 is provided to protrude from the band 20 to the wrist W side, the injection part 150 rarely comes into contact with the wrist W of a wearer, and thus it is possible to reduce discomfort felt by the wearer. In addition, since the injection operation of injecting air into the inflatable portion 40 is performed on the support plate 22 having the high hardness, the injection operation is facilitated. Note that a position at which the injection part 150 is disposed is preferably disposed on the band 20. However, the position is not particularly limited.

The hole portion 150*b* formed in the injection part 150 penetrates the vertical wall part 152 in a direction intersecting with an extending direction of the injection part 150 (vertical direction of FIG. 10(B)). The hole portion 150*b* allows air to be taken into the housing space 150*a*. For example, when the inflatable portion 40 is inflated, as illustrated in FIG. 11(B), a finger is placed to grip the injection part 150, and the injection part 150 is deformed while the hole portion 150*b* is blocked with the finger. By this operation, air in the housing space 150*a* is sent to a lumen 62 of the tube body 60 communicating with the housing space 150*a*. As described below, the communication portion 71 opens by the air sent to the lumen 62 of the tube body 60, so that the lumen 62 of the tube body 60 and the inflatable space 40*a* of the inflatable portion 40 communicate with each other.

As described above, the hole portion 150*b* of the injection part 150 is formed in the vertical wall part 152. For this reason, a pressing force at the time of deforming the injection part 150 on the vertical wall part 152 becomes relatively difficult to be transmitted to the puncture site P positioned on the inner surface side of the band 20 (see FIG. 9). Therefore, it is possible to suitably prevent a situation in which the puncture site P is pressed more than necessary by an injection operation of injecting air into the inflatable portion 40. In addition, as described above, since the pressing force for deforming the injection part 150 becomes relatively difficult to be transmitted to the puncture site P, when the inflatable portion 40 is inflated, the wearer can relatively accurately detect only a pressing force applied to the puncture site P by the inflatable portion 40. In this way, it is possible to inject an optimum amount of air for hemostasis of the puncture site P into the inflatable portion 40 based on a pressing force felt by the wearer. Further, since the hole portion 150*b* is formed in the vertical wall part 152, when compared to a case in which the hole portion 150*b* is formed in the upper face part 153, a possibility that the hole portion 150*b* will come into contact with a surrounding article, etc. and be blocked decreases. For this reason, it is possible to prevent the injection part 150 from being unintentionally deformed to inadvertently inject air into the inflatable portion 40.

Note that the number of hole portions 150*b* formed in the injection part 150, a position and a shape of the hole portion 150*b*, etc. are not particularly limited and may be appropriately changed as long as air can be injected into the inflatable portion 40 from the injection part 150.

For example, the injection part 150 may be made of an elastomer material such as silicone rubber or latex rubber, a thermoplastic plastic material such as polypropylene or polyethylene, or various thermoplastic elastomer materials having both properties of these materials. Note that the injection part 150 is formed to have a relatively thin wall thickness such that a movement operation (rotation operation) of the tube body 60 can be performed from the outside via fingers, etc. in a state in which the injection part 150 covers a periphery of the tube body 60 and folding is allowed in the vertical direction (vertical direction in FIG. 10(B)).

For example, the injection part 150 can be connected to the band 20 by welding or attaching the bottom face part 151 to the support plate holding portion 21*a* (see FIG. 10(B)).

Figure 13:
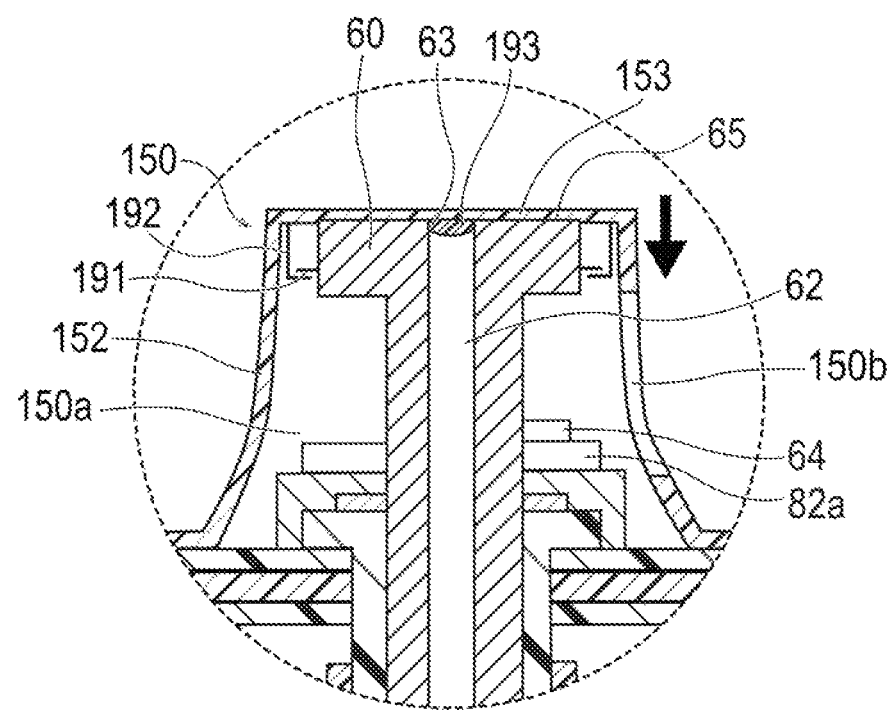
FIG. 13 is a partially enlarged cross-sectional view of the hemostatic device according to Modification 1.

As illustrated in FIG. 13, a first stopper 191 is disposed on the grip portion 65 of the tube body 60, and a second stopper 192 is disposed on an inner surface side of the upper face part 153 of the injection part 150. The first stopper 191 is formed in a shape extending in a direction orthogonal to an axial direction of the tube body 60, and the second stopper 192 is formed in an L-shape that can be hooked on the second stopper 192.

In Modification 1, the injection part 150 can be folded, that is, pressed in the direction of the illustrated arrow shown in FIG. 13, when an operation of injecting air by the injection part 150 is not performed. When the injection part 150 is folded, a distal portion of the second stopper 192 is hooked on the first stopper 191. In this way, the injection part 150 maintains a folded state. In this instance, since the proximal end opening 63 of the tube body 60 is covered with an inner surface of the upper face part 153 of the injection part 150, even when the positions of the hole portion 61 and the communication portion 71 overlap with each other, it is possible to suitably prevent air from leaking from the proximal end opening 63. When a state in which the injection part 150 is folded is released, the second stopper 192 is removed from the first stopper 191 by operating the injection part 150 using fingers, etc.

A sealing member 193 that seals the proximal end opening 63 of the tube body 60 at the time of folding the injection part 150 is disposed on the inner surface of the upper face part 153 of the injection part 150. The sealing member 193 is formed of a convex member inserted into the lumen 62 of the tube body 60 at the time of folding the injection part 150. For example, the sealing member 193 may be formed of a known elastic member. In addition, for example, the sealing member 193 may be configured by securing a portion including a member separate from the injection part 150 to the injection part 150, or may be configured by a part of the injection part 150. In addition, a specific shape of the sealing member 193 is not limited to an illustrated shape. For example, the sealing member 193 may be formed in a shape for sealing the proximal end opening 63 by coming into close contact with the grip portion 65 (the proximal end opening 63 and a periphery thereof) at the time of folding the injection part 150.

Note that for example, the first stopper 191 and the second stopper 192 may be configured as a lock mechanism that restricts movement so that the tube body 60 may not rotate by securing the tube body 60 to the injection part 150 while maintaining the state in which the injection part 150 is folded, or may be configured as a lock mechanism that restricts movement so that the tube body 60 may not rotate by securing the injection part 150 to the band 20.

Next, a description will be given of an operation example of the decompression adjustment mechanism 60A and the injection part 150.

FIG. 10(A) and FIG. 10(B) illustrate a state before the inflatable portion 40 is inflated. In this state, the hole portion 61 of the tube body 60 is not disposed at a position overlapping the communication portion 71 of the cover portion 70, and thus the communication portion 71 is in a closed state.

Figure 11A:
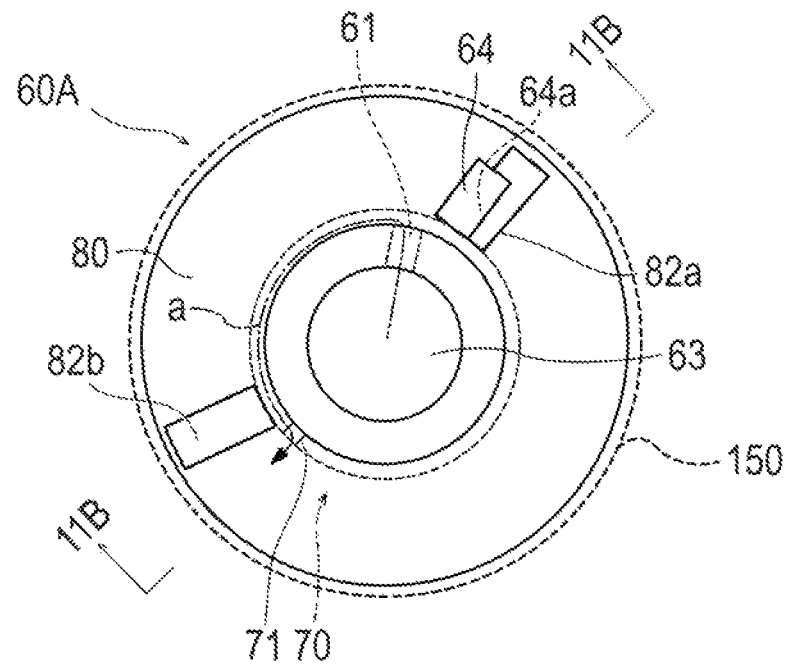
FIG. 11(A) is a plan view of the tube body and the cover portion according to Modification 1.
Figure 11B:
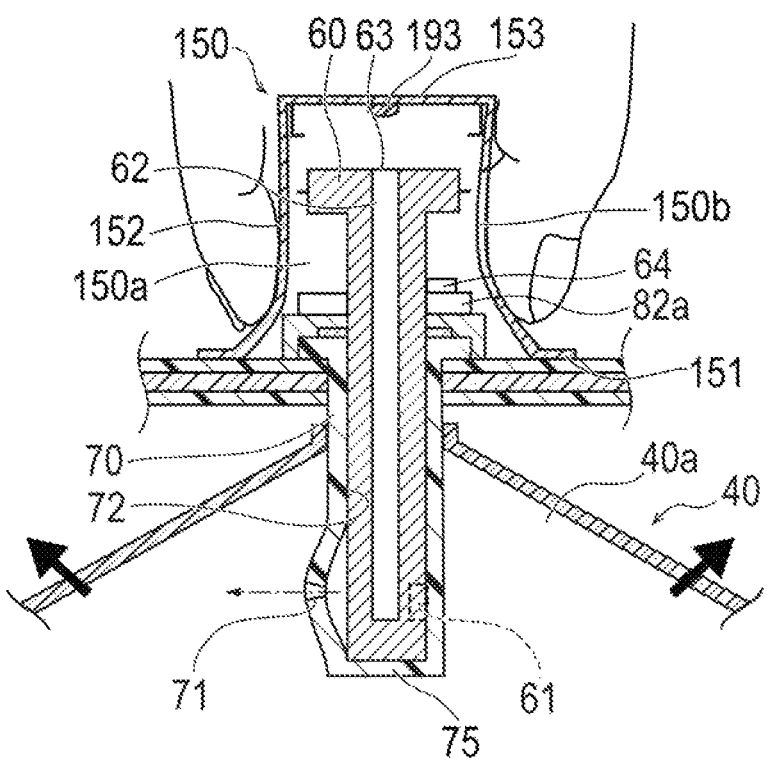
FIG. 11(B) is a cross-sectional view taken along 11B-11B line illustrated in FIG. 11(A).

FIG. 11(A) and FIG. 11(B) illustrate an aspect of the disclosure when the injection part 150 is operated to inflate the inflatable portion 40.

When air is sent to the tube body 60 by pressing and deforming the injection part 150, the air is released from the hole portion 61 via the lumen 62 of the tube body 60. When the air is released from the hole portion 61, a slight clearance portion is formed between the outer surface of the tube body 60 and the inner surface of the cover portion 70. The air moves to the communication portion 71 via the clearance portion formed around the outer surface of the tube body 60 (see an arrow "a" in FIG. 11(A)). When the air reaches the communication portion 71, the slit forming the communication portion 71 is opened to allow communication between the lumen 62 of the tube body 60 and the inflatable space 40a of the inflatable portion 40. Then, the inflatable portion 40 is inflated by injecting the air into the inflatable space 40a of the inflatable portion 40. Hence, the hole portion 61 and the communication portion 71 do not have to be overlapping in order to inflate inflatable portion 40. On the other hand though, the hold portion 61 and the communication portion 71 have to be overlapping in order to deflate the inflatable portion 40.

When pressing of the injection part 150 is released after the inflatable portion 40 is inflated, the injection part 150 is elastically transformed to return to an original shape. In this instance, when the lumen 62 of the tube body 60 becomes negative pressure with respect to the inflatable space 40a, the communication portion 71 is closed, and a communication state between the inflatable space 40a of the inflatable portion 40 and the housing space 150a of the injection part 150 is blocked. Further, since the inner surface of the cover portion 70 and the outer surface of the tube body 60 are in close contact with each other without any gap due to the internal pressure of the inflatable portion 40, it is possible to prevent occurrence of backflow of air from the inflatable portion 40 side to the injection part 150 side.

Figure 12A:
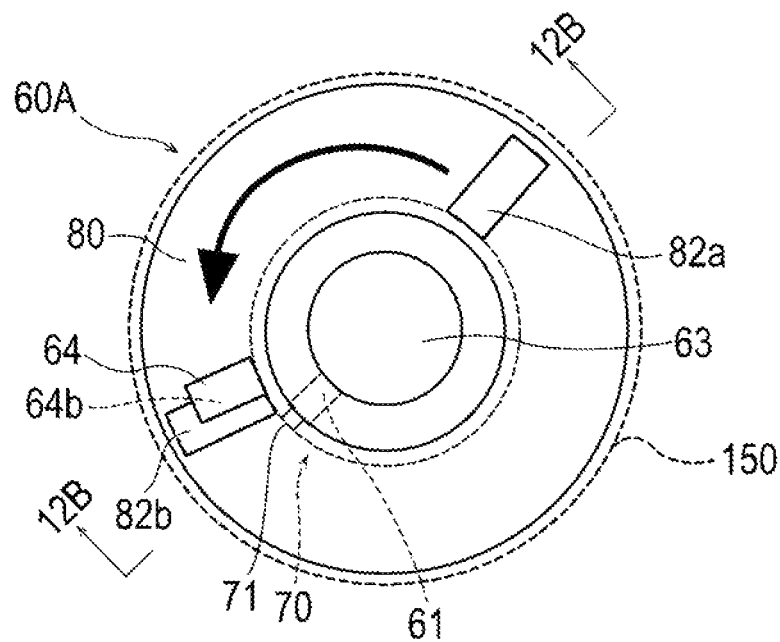
FIG. 12(A) is a plan view of the tube body and the cover portion according to Modification 1.
Figure 12B:
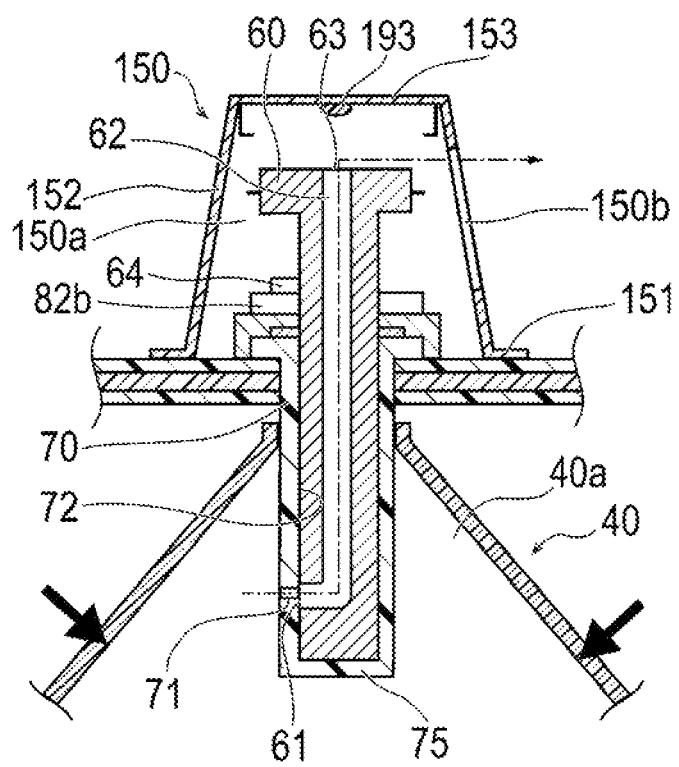
FIG. 12(B) is a cross-sectional view taken along 12B-12B line illustrated in FIG. 12(A).

FIG. 12(A) and FIG. 12(B) illustrate an aspect of the disclosure when the decompression operation of the tube body 60 is performed.

When the tube body 60 is rotated to overlap the positions of the hole portion 61 and the communication portion 71, the slit forming the communication portion 71 is pressed toward the hole portion 61 side by the internal pressure of the inflatable portion 40 to open the slit. The communication portion 71 allows communication between the lumen 62 of the tube body 60 and the inflatable space 40a of the inflatable portion 40. Air in the inflatable portion 40 is discharged to the outside via the lumen 62 of the tube body 60, the housing space 150a of the injection part 150, and the hole portion 150b of the injection part 150. Since an amount of air discharged from the inflatable portion 40 when the positions of the hole portion 61 and the communication portion 71 overlap each other is controlled based on a shape and a size (dimension) of the slit forming the communication portion 71, it is possible to quantitatively control the discharge amount of air, and to appropriately discharge a desired amount of air.

When the decompression operation of the inflatable portion 40 is completed, the tube body 60 is rotated to adjust the positional relation between the hole portion 61 and the communication portion 71 so that the hole portion 61 and the communication portion 71 do not overlap each other.

As described above, the hemostatic device 100 according to Modification 1 has the injection part 150 which can be elastically transformed and can inject air into the inflatable portion 40. In addition, the tube body 60 connects the inflatable space 40a and the housing space 150a of the injection part 150 to each other. In addition, the communication portion 71 allows communication between the inflatable space 40a and the housing space 150a by virtue of the air discharged from the hole portion 61 of the tube body 60 when air is injected into the inflatable portion 40 from the injection part 150.

According to the hemostatic device 100, it is possible to inflate the inflatable portion 40 by a simple operation without using a dedicated instrument separate from the hemostatic device 100. In addition, even when the decompression operation of the inflatable portion 40 is performed, it is unnecessary to use the dedicated instrument separate from the hemostatic device 100. Therefore, it is possible to eliminate the need to carry the dedicated instrument separate from the hemostatic device 100 or an effort to connect the dedicated instrument to the hemostatic device 100, and it is possible to prevent occurrence of a situation in which inflation and decompression of the inflatable portion 40 may not be performed by losing the dedicated instrument.

Modification 2

Figure 14A:
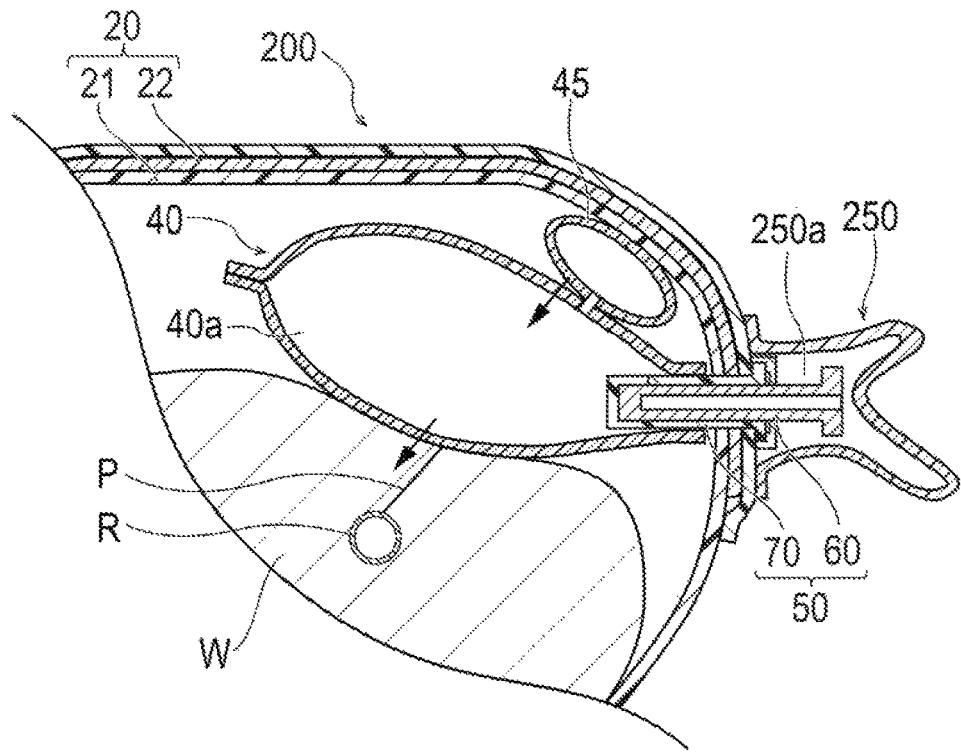
FIG. 14(A) is a partially enlarged cross-sectional view of a hemostatic device according to Modification 2 illustrating a state in which an inflatable portion is inflated.
Figure 14B:
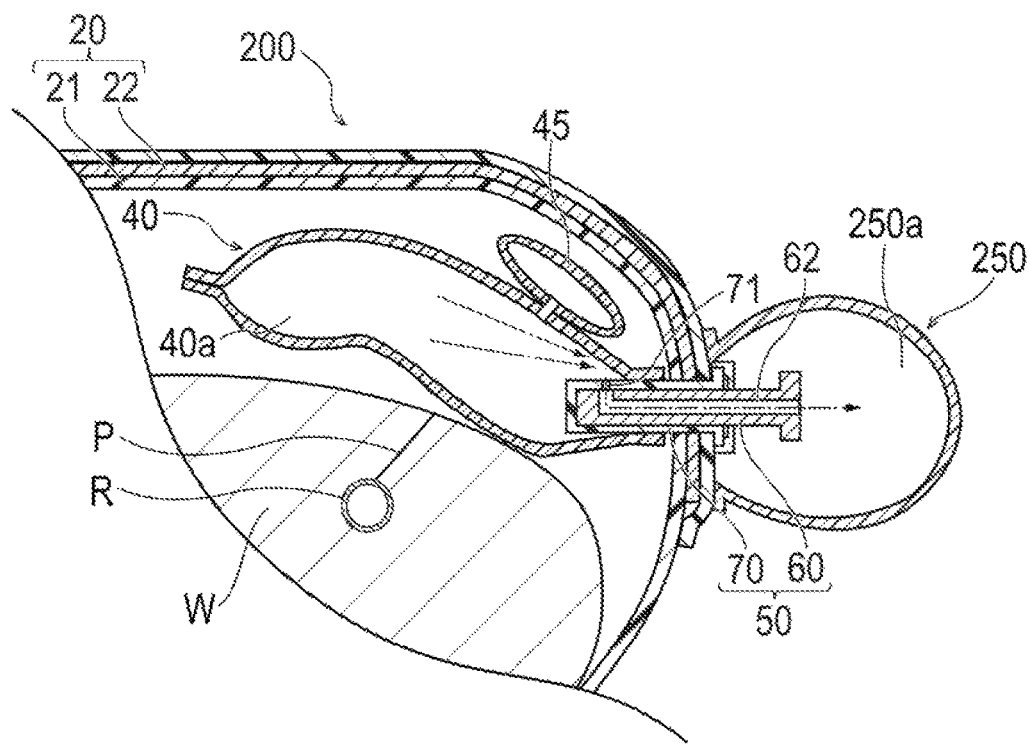
FIG. 14(B) is a diagram illustrating an aspect when the inflatable portion is decompressed and adjusted.

FIG. 14(A) and FIG. 14(B) are diagrams for description of a hemostatic device 200 according to Modification 2 of the disclosure.

As illustrated in FIG. 14(A), the hemostatic device 200 according to Modification 2 includes a gas collecting portion 250. The hemostatic device 200 is configured similarly to the hemostatic device 100 according to the exemplary embodiment of FIG. 1, except that the hemostatic device 200 includes the gas collecting portion 250. Although not illustrated, the hemostatic device 200 includes the injection part 50 that inflates the inflatable portion 40 using the syringe, etc.

The gas collecting portion 250 is formed of a membrane-shaped member that covers the proximal side of the tube body 60. The gas collecting portion 250 partitions an airtight housing space (lumen) 250a around the tube body 60. For example, the housing space 250a may be formed such that the volume thereof at the time of inflating most (the volume at the time of maximum inflation) is smaller than the volume of the inflatable portion 40 at the time of maximum inflation. Since decompression of the inflatable portion 40 is adjusted within a range in which desired compression can be achieved without discharging all of the air in the inflatable portion 40, it is possible to prevent the gas collecting portion 250 from becoming unnecessarily large by forming the volume of the housing space 250a as described above.

Examples of a material contained in the gas collecting portion 250 may include the same material as that of the inflatable portion 40.

As illustrated in FIG. 14(A), in a state in which air is not discharged from the inflatable portion 40, the gas collecting portion 250 is in a deflated state (contracted state). As illustrated in FIG. 14(B), when the communication portion 71 is opened by overlapping the positions of the hole portion 61 of the tube body 60 and the communication portion 71 of the cover portion 70, air is discharged from the inflatable portion 40. The air discharged from the inflatable portion 40 moves into the housing space 250a corresponding to the outside of the inflatable space 40a. For example, when the gas collecting portion 250 is pressed in a state in which air is housed in the housing space 250a, air can be sent to the inflatable portion 40 again. For this reason, even in a case in which air is excessively extracted from the inflatable portion 40 after inflation using the decompression adjustment mechanism 60A or in a case in which air is excessively extracted from the inflatable portion 40 using the injection part 50, it is possible to send air to the inflatable portion 40 again by a simple operation, and to readjust the internal pressure of the inflatable portion 40. In addition, the wearer, the doctor, etc. may easily confirm an extent to which decompression of the inflatable portion 40 progresses by visually checking a degree of inflation of the gas collecting portion 250.

As described above, since the hemostatic device 200 according to Modification 2 includes the gas collecting portion 250, it is possible to finely adjust the internal pressure of the inflatable portion by a simple operation. In addition, in the hemostatic device 200 according to Modification 2, the gas collecting portion 250 has a simple configuration, and thus it is possible reduce manufacturing cost and facilitate manufacturing work.

Modification 3

Figure 15A:
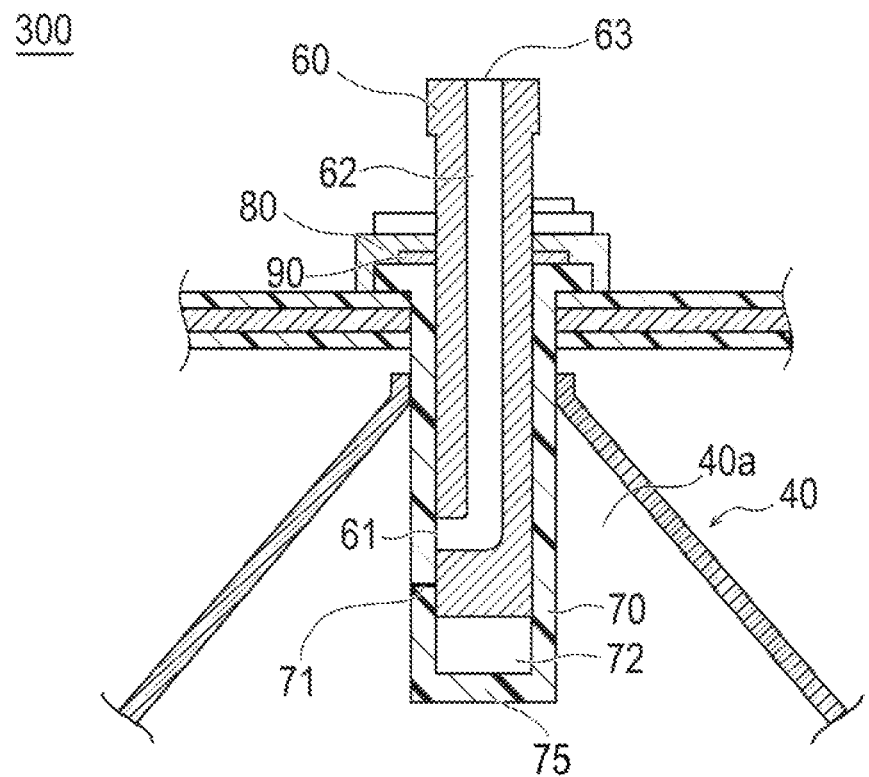
FIG. 15(A) is a cross-sectional view for description of an operation example of a hemostatic device according to Modification 1 illustrating a state before a hole portion of a tube body and a communication portion of a cover portion are positioned.
Figure 15B:
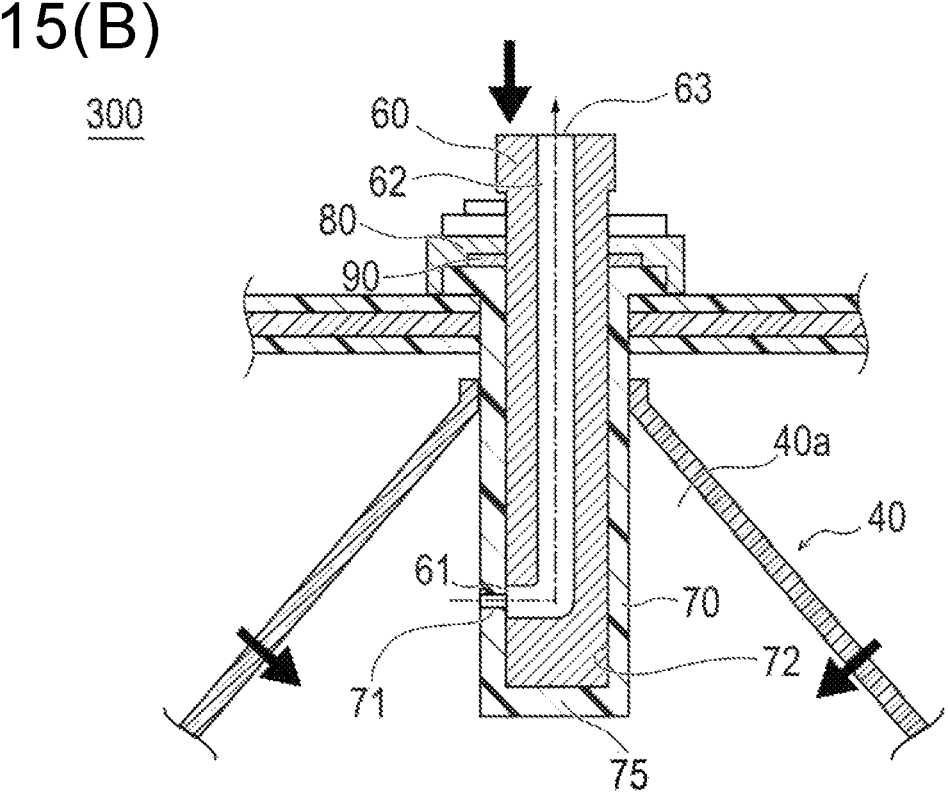
FIG. 15(B) is a diagram illustrating an aspect when the hole portion of the tube body and the communication portion of the cover portion are positioned.

FIG. 15(A) and FIG. 15(B) are diagrams for description of a hemostatic device 300 according to Modification 3.

As illustrated in FIG. 15(A), the hemostatic device 300 according to Modification 3 is different from the exemplary embodiment and the respective modifications described above in that the tube body 60 is movable with respect to the cover portion 70 along an axial direction of the cover portion 70 (vertical direction in the figure).

As illustrated in FIG. 15(A) and FIG. 15(B), when the decompression operation of the inflatable portion 40 is performed, the tube body 60 is moved to a distal side of the cover portion 70 (lower side in the figure) to superimpose the positions of the hole portion 61 and the communication portion 71. By performing this operation, it is possible to discharge air from the inflatable portion 40 by opening the communication portion 71. Note that the bottom face part 75 is provided on the tube body 60 to prevent the tube body 60 from falling from the cover portion 70 when the tube body 60 is moved in the axial direction.

As described above, a mechanism for controlling movement of the tube body 60 for superimposing the positions of the hole portion 61 and the communication portion 71 is not limited to a mechanism for controlling rotational movement of the tube body 60, and may correspond to a mechanism for controlling movement of the tube body 60 in the axial direction as in the present modification.

Note that the hemostatic device 300 shown in Modification 3 illustrates a configuration not including the injection part for injecting air and the lock mechanism that restricts movement of the tube body 60. However, it is possible to adopt a configuration including the injection part and the lock mechanism similar to the exemplary embodiment and the respective modifications.

Even though the hemostatic device according to the disclosure herein has been described above through the exemplary embodiment and various modifications, the invention is not limited only to the respective configurations described above, and can be appropriately changed based on the description of claims.

For example, each portion included in the hemostatic device may be replaced with a portion having an arbitrary configuration capable of exerting the same function. In addition, an arbitrary component may be added.

In addition, the disclosure is not limited to the hemostatic device used by being mounted on the wrist, and may be applied to a hemostatic device used by being mounted on a leg, etc.

In addition, in the exemplary embodiment, a description has been given of a case in which the hemostatic device includes the auxiliary pressing portion. However, the hemostatic device may not include the auxiliary pressing portion.

In addition, movement of the tube body is not limited to rotation with respect to the cover portion or movement along the axial direction (movement in the vertical direction) illustrated in the exemplary embodiment. For example, the positions of the hole portion and the communication portion may be aligned by combining rotation of the tube body and movement in the axial direction. In addition, the tube body and the cover portion may be controllable so that the positions of the hole portion and the communication portion overlap each other by relative movement of the tube body and the cover portion. For example, the cover portion may be configured to be movable with respect to the tube body, or both the cover portion and the tube body may be configured to be movable.

In addition, a configuration of the tube body and the cover portion is not particularly limited as long as the lumen of the inflatable portion and the outside can communicate with each other when the positions of the hole portion and the communication portion overlap each other. For example, use of additional members (the valve body, the lid member, etc.) described in the exemplary embodiment may be omitted as appropriate.

The detailed description above describes embodiments and modifications of a hemostatic device and method representing examples of the inventive hemostatic device and method disclosed here. The invention is not limited, however, to the precise embodiments and modifications described. Various changes, modifications and equivalents can be effected by one skilled in the art without departing from the spirit and scope of the invention as defined in the accompanying claims. It is expressly intended that all such changes, modifications and equivalents which fall within the scope of the claims are embraced by the claims.

What is claimed is:

1. A hemostatic device comprising:
a band adapted to be wrapped around a limb of a patient at a site on the limb wherein bleeding is to be stopped;
securing means for securing the band to the limb in a wrapped state;
an inflatable portion connected to the band and adapted to be inflated by being injected with gas;
a tube body configured to communicate between a lumen of the inflatable portion and an outside; and
a cover portion configured to cover the tube body in the inflatable portion,
wherein the tube body has a hole portion that opens in the inflatable portion,
wherein the cover portion has a communication portion that is disposed to cover the hole portion and allows communication between the hole portion and the lumen of the inflatable portion by being positioned to overlap the hole portion, and
wherein the tube body is rotatable relative to the cover portion so that a positional relationship between the communication portion and the hole portion is controllable.

2. The hemostatic device according to claim 1, wherein the communication portion is disposed at a same position as a position of the hole portion in a cross section perpendicular to an axial center of the tube body.

3. The hemostatic device according to claim 1, further including a lock mechanism restricts movement of the tube body relative to the cover portion.

4. The hemostatic device according to claim 3, wherein the lock mechanism includes a first member disposed on the tube body and at least one second member provided on a support body disposed on a proximal side of the cover portion and configured to be engaged with and separated from the first member.

5. The hemostatic device according to claim 4, wherein the at least one second member provided on the support body includes a first second member and a second second member provided on the support body and the tube body is rotatable relative to the cover portion within a rotation range between the first second member and the second second member.

6. The hemostatic device according to claim 1, wherein the communication portion corresponds to a slit that opens at a time of being aligned with the hole portion.

7. The hemostatic device according to claim 1, further comprising:
   an injection part which is elastically deformable and configured to inject gas into the inflatable portion,
   wherein the tube body connects the lumen of the inflatable portion and a lumen of the injection part to each other, and
   wherein the communication portion allows communication between the lumen of the inflatable portion and the lumen of the injection part by gas discharged from the hole portion when gas is injected into the inflatable portion from the injection part.

8. The hemostatic device according to claim 7, wherein the injection part is disposed on an outer surface of the band.

9. A hemostatic device comprising:
   a flexible band configured to be wrapped around a hemostasis-requiring site of a limb;
   a securing portion that secures the band in a state where the band is wrapped around the limb;
   an inflatable portion configured to overlap with the band and inflate when a fluid is injected into the inflatable portion; and
   a tube body and a cover portion;
   wherein the tube body includes a hole portion opening into an interior of the inflatable portion and the cover portion is disposed over the tube body so as to cover the hole portion and be in close contact with the tube body; and
   wherein the cover portion includes a communication portion;
   wherein the tube body is movable relative to the cover portion between a position in which the hole portion of the tube body overlaps with the communication portion of the cover portion and a position in which the hole portion of the tube body does not overlap with the communication portion of the cover portion, the tube body and the cover portion being configured such that air is discharged from the inflatable portion when the tube body is in the position in which the hole portion of the tube body overlaps with the communication portion of the cover portion, and such that air is not discharged from the inflatable portion when the tube body is in the position in which the hole portion of the tube body does not overlap with the communication portion of the cover portion.

10. The hemostatic device according to claim 9, further comprising an elastically deformable injection part configured to inject gas into the inflatable portion;
    wherein the tube body connects the interior of the inflatable portion and an interior of the injection part; and
    wherein the communication portion of the cover portion is adapted to have an open state when gas is injected into the inflatable portion from the injection part thereby allowing communication between the interior of the inflatable portion and an interior of the injection part.

11. The hemostatic device according to claim 10, further including a lock mechanism configured to restrict movement of the tube body relative to the cover portion.

12. The hemostatic device according to claim 11, wherein the lock mechanism includes a first member disposed on the tube body and at least one second member provided on a support body disposed on a proximal side of the cover portion.

13. The hemostatic device according to claim 12, wherein the at least one second member provided on the support body includes a first second member and a second second member provided on the support body and the tube body is rotatable relative to the cover portion within a rotation range between the first second member and the second second member.

* * * * *